(12) United States Patent
Rainer

(10) Patent No.: US 7,052,892 B2
(45) Date of Patent: May 30, 2006

(54) REGULATION OF HUMAN WEE1-LIKE SERINE/THREONINE PROTEIN KINASE

(75) Inventor: Köhler H. Rainer, Beverly, MA (US)

(73) Assignee: Bayer HealthCare AG, Leverkusen (DE)

( * ) Notice: Subject to any disclaimer, the term of this patent is extended or adjusted under 35 U.S.C. 154(b) by 201 days.

(21) Appl. No.: 10/470,726

(22) PCT Filed: Jan. 30, 2002

(86) PCT No.: PCT/EP02/00912

§ 371 (c)(1),
(2), (4) Date: Jul. 31, 2003

(87) PCT Pub. No.: WO02/061057

PCT Pub. Date: Aug. 8, 2002

(65) Prior Publication Data

US 2004/0077049 A1 Apr. 22, 2004

Related U.S. Application Data

(60) Provisional application No. 60/334,974, filed on Dec. 4, 2001, provisional application No. 60/324,051, filed on Sep. 24, 2001, provisional application No. 60/265,352, filed on Feb. 1, 2001.

(51) Int. Cl.
*C12N 9/12* (2006.01)
*C12N 1/20* (2006.01)
*C12N 15/00* (2006.01)
*C07H 21/04* (2006.01)
*C07K 1/00* (2006.01)

(52) U.S. Cl. .......................... 435/194; 6/252.3; 6/320.1; 6/325; 536/23.2; 530/350

(58) Field of Classification Search ................ 435/194, 435/6, 252.3, 320.1, 325; 530/350; 536/23.2
See application file for complete search history.

(56) References Cited

OTHER PUBLICATIONS

Watanabe et al.(1995) Regulation of the human WEE1Hu CDK tyrosine 15-kinase during the cell cycle.EMBO J 1;14(9):1878-91.
McGowan and Russell (1995) Cell cycle regulation of human WEE1. EMBO J 14(10):2166-75.
Hanks and Hunter (1995) Protein kinases 6. The eukaryotic protein kinase superfamily: kinase (catalytic) domain stucture and classification. FASEB J 9(8):576-96.
Du H. et al. Database EMBL 'Online' "The sequence of Homo sapiens PAC clone RP5-894a 10" Database accession No. 095017.
Bagguley C. Database EMBL 'Online' "Human DNA sequence from clone RP5-916011" Database accession No. AL136146.10
Mueller Paul R et al: "Cell cycle regulation of a Xenopus Weel-like kinase." Molecular Biology of the Cell, vol. 6, No. 1, 1995, pp. 119-134.
Tiranti Valeria et al: "Cloning of human and rat cDNAs encoding the mitochondrial single-stranded DNA-binding protein (SSB)." Gene (Amsterdam), vol. 126, No. 2, 1993, pp. 219-225.

*Primary Examiner*—Maryam Monshipouri
(74) *Attorney, Agent, or Firm*—Banner & Witcoff, Ltd.

(57) ABSTRACT

Reagents that regulate human WEE1-like serine/threonine protein kinase and reagents which bind to human WEE1-like serine/threonine protein kinase gene products can play a role in preventing, ameliorating, or correcting dysfunctions or diseases including, but not limited to, cancer, peripheral and central nervous system disorders, genitourinary disorders, cardiovascular disorders, and COPD.

17 Claims, 11 Drawing Sheets

Fig. 1

```
atggatgacaaagatattgacaaagaactaaggcagaaattaaacttttccta
ttgtgaggagactgagattgaagggcagaagaaagtagaagaaagcagggagg
cttcgagccaaaccccagagaagggtgaagtgcaggattcagaggcaaagggt
acaccaccttggactcccttagcaacgtgcatgagctcgacacatcttcgga
aaaagacaaagaaagtccagatcagatttgaggactccagtgtcacaccctc
tcaaatgtcctgagacaccagcccaaccagacagcaggagcaagctgctgccc
agtgacagcccctctactcccaaaaccatgctgagccggttggtgatttctcc
aacagggaagcttccttccagaggccctaagcatttgaagctcacacctgctc
ccctcaaggatgagatgacctcattggctctggtcaatattaatcccttcact
ccagagtcctataaaaaattatttcttcaatctggtggcaagaggaaaataag
aggagatcttgaggaagctggtccagaggaaggcaagggagggctgcctgcca
agagatgtgtttacgagaaaccaacatggcttccgctatgaaaaagaattc
ttggaggttgaaaaaattggggttggcgaatttggtacagtctacaagtgcat
taagaggctggatggatgtgtttatgcaataaagcgctctatgaaaacttta
cagaattatcaaatgagaattcggctttgcatgaagtttatgctcacgcagtg
cttgggcatcaccccatgtggtacgttactattcctcatgggcagaagatga
ccacatgatcattcagaatgaatactgcaatggtgggagtttgcaagctgcta
tatctgaaaacactaagtctggcaatcatttgaagagccaaaactcaaggac
atccttctacagatttcccttggccttaattacatccacaactctagcatggt
acacctggacatcaaacctagtaatatattcatttgtcacaagatgcaaagtg
aatcctctggagtcatagaagaagttgaaaatgaagctgattggtttctctct
gccaatgtgatgtataaaattggtgacctgggccacgcaacatcaataaacaa
acccaaagtggaagaaggagatagtcgcttcctggctaatgagatttgcaag
aggattaccggcaccttcccaaagcagacatatttgccttgggattaacaatt
gcagtggctgcaggagcagagtcattgcccaccaatggtgctgcatggcacca
tatccgcaagggtaactttccggacgttcctcaggagctctcagaagctttt
ccagtctgctcaagaacatgatccaacctgatgccgaacagagaccttctgca
gcagctctggccagaaatacagttctccggccttccctgggaaaaacagaaga
gctccaacagcagctgaatttggaaaagttcaagactgccacactggaaaggg
aactgagagaagcccagcaggcccagtcaccccagggatatacccatcatggt
gacactggggtctctgggacccacacaggatcaagaagcacaaaacgcctggt
gggaggaaagagtgcaaggtcttcaagctttacc
```

Fig. 2

```
MDDKDIDKELRQKLNFSYCEETEIEGQKKVEESREASSQTPEKGEVQDSEAKG
TPPWTPLSNVHELDTSSEKDKESPDQILRTPVSHPLKCPETPAQPDSRSKLLP
SDSPSTPKTMLSRLVISPTGKLPSRGPKHLKLTPAPLKDEMTSLALVNINPFT
PESYKKLFLQSGGKRKIRGDLEEAGPEEGKGGLPAKRCVLRETNMASRYEKEF
LEVEKIGVGEFGTVYKCIKRLDGCVYAIKRSMKTFTELSNENSALHEVYAHAV
LGHHPHVVRYYSSWAEDDHMIIQNEYCNGGSLQAAISENTKSGNHFEEPKLKD
ILLQISLGLNYIHNSSMVHLDIKPSNIFICHKMQSESSGVIEEVENEADWFLS
ANVMYKIGDLGHATSINKPKVEEGDSRFLANEILQEDYRHLPKADIFALGLTI
AVAAGAESLPTNGAAWHHIRKGNFPDVPQELSESFSSLLKNMIQPDAEQRPSA
AALARNTVLRPSLGKTEELQQQLNLEKFKTATLERELREAQQAQSPQGYTHHG
DTGVSGTHTGSRSTKRLVGGKSARSSSFT
```

Fig 3

MRTAMSCGGGLVQRLDFSSSDEEDGLSNGINEGPQKGSPVSSWRTNNCPFPIT
PQRNERELSPTQELSPSSDYSPDPSVGAECPGTPLHYSTWKKLKLCDTPYTPK
SLLYKTLPSPGSRVHCRGQRLLRFVAGTGAELDDPSLVNINPFTPESYRQTHF
QPNGKRKERPEDDCRTDRQMKYAEKEHPAVFQSKRFVLRETNMGSRYKTEFLE
IEKIGAGEFGSVFKCVKRLDGCFYAIKRSKKPLAGSTDEQLALREVYAHAVLG
HHPHVVRYYSAWAEDDHMIIQNEYCNGGSLQDLIVDNNKEGQFVLEQELKEIL
LQVSMGLKYIHGSGLVHMDIKPSNIFICRKQTELGQEESDGEDDLSSGSVLYK
IGDLGHVTSILNPQVEEGDSRFLANEILQEDYSQLPKADIFALGLTIALAAGA
APLPCNEDSWHHIRKGNLPHVPQLLTPVFLALLKLLVHPDPVMRPPAASLAKN
SVLRRCVGKAAQLQKQLNVEKFKTAMLERELKAAKLAQTSGKDECSDLPPMSG
FSCRGRKRLVGAKNTRSLSFTCGGY

Fig. 4

TTTGAGATAGTGATTTTATTTCCTTTGGCTATATAACTGGAAGAGAAGAGGGA
CAGCTTGATTGTATAATAGTTGTTTTTTTCTTCAAAGAGTTTTCCATCCTTCT
CATCGGGGCTTCTCTTTTGTCATCCTCATTCAGACCATGCTGAGCCGGTTGGT
GATTTCTCCAACAGGGAAGCTTCCTTCCAGAGGCCCTAAGCATTTGAAGCTCA
CACCTGCTCCCCTCAAGGATGAGATGACCTCATTGGCTCTGGTCAATATTAAT
CCCTTCACTCCAGAGTCCTATAAAAAATTATTTCTTCAATATCTATCCTGTCA
TTTTTTTTTCAGGTAATATA

Fig. 5

```
atggatgacaaagatattgacaaagaactaaggcagaaattaaacttttccta
ttgtgaggagactgagattgaagggcagaagaaagtagaagaaagcagggagg
cttcgagccaaaccccagagaagggtgaagtgcaggattcagaggcaaagggt
acaccaccttggactccccttagcaacgtgcatgagctcgacacatcttcgga
aaaagacaaagaaagtccagatcagattttgaggactccagtgtcacaccctc
tcaaatgtcctgagacaccagcccaaccagacagcaggagcaagctgctgccc
agtgacagccctctactcccaaaaccatgctgagccggttggtgatttctcc
aacagggaagcttccttccagaggccctaagcatttgaagctcacacctgctc
ccctcaaggatgagatgacctcattggctctggtcaatattaatcccttcact
ccagagtcctataaaaattatttcttcaatctggtggcaagaggaaaataag
aggagatcttgaggaagctggtccagaggaaggcaagggagggctgcctgcca
agagatgtgttttacgagaaaccaacatggcttcccgctatgaaaagaattc
ttggaggttgaaaaaattggggttggcgaatttggtacagtctacaagtgcat
taagaggctggatggatgtgtttatgcaataaagcgctctatgaaaactttta
cagaattatcaaatgagaattcggctttgcatgaagtttatgctcacgcagtg
cttgggcatcaccccatgtggtacgttactattcctcatgggcagaagatga
ccacatgatcattcagaatgaatactgcaatggtgggagtttgcaagctgcta
tatctgaaaacactaagtctggcaatcatttgaagagccaaaactcaaggac
atccttctacagatttcccttggccttaattacatccacaactctagcatggt
acacctggacatcaaacctagtaatatattcatttgtcacaagatgcaaagtg
aatcctctggagtcatagaagaagttgaaaatgaagctgattggtttctctct
gccaatgtgatgtataaaattggtgacctgggccacgcaacatcaataaacaa
acccaaagtggaagaaggagatagtcgcttcctggctaatgagatttgcaag
aggattaccggcaccttcccaaagcagacatatttgccttgggattaacaatt
gcagtggctgcaggagcagagtcattgcccaccaatggtgctgcatggcacca
tatccgcaagggtaacttccggacgttcctcaggagctctcagaaagctttt
ccagtctgctcaagaacatgatccaacctgatgccgaacagagaccttctgca
gcagctctggccagaaatacagttctccggccttccctgggaaaaacagaaga
gctccaacagcagctgaatttggaaaagttcaagactgccacactggaaggg
aactgagagaagcccagcaggcccagtcaccccagggatatacccatcatggt
gacactggggtctctgggacccacacaggatcaagaagcacaaaacgcctggt
gggaggaaagagtgcaaggtcttcaagctttacctacacacagatacttacca
tgaattacaatggtctgcggtattcagtacagccccatgctgtcaggtttgca
gcctggaagcagcaggccacaccacagagccgaggtgtgtccaggctccacca
tctaggtcgtcaaagtacattctgtggtgttcgtacagcaacaaaatcgccta
atgacgcaatcctcagaccttaccctgttgttaaggtacttcgtcagtttgta
agacatgagtccgaaacaactaccagtttggttcttgaaagatccctgaatcg
tgtgcacttactgggcgagtgggtcaggaccctgtcttgagacaggtggaag
gaaaaaatccagtcacaatatttctctagcaactaatgagatgtggcgatca
ggggatagtgaagtttaccaactgggtgatgtcagtcaaaagacaacatggca
cagaatatcagtattccggccaggcctcagagacgtggcatatcaatatgtga
aaaggggtctcgaatttatttggaagggaaaatagactatggtgaatacatg
gataaaaataatgtgaggcgacaagcaacaacaatcatagctgggatcctatc
tgtaactaaaaaaccaccaccagtggatggcactcttggcttttccacagtg
atattaattcgagtagtttgttctga
```

Fig 6

```
MDDKDIDKELRQKLNFSYCEETEIEGQKKVEESREASSQTPEKGEVQDSEAKG
TPPWTPLSNVHELDTSSEKDKESPDQILRTPVSHPLKCPETPAQPDSRSKLLP
SDSPSTPKTMLSRLVISPTGKLPSRGPKHLKLTPAPLKDEMTSLALVNINPFT
PESYKKLFLQSGGKRKIRGDLEEAGPEEGKGGLPAKRCVLRETNMASRYEKEF
LEVEKIGVGEFGTVYKCIKRLDGCVYAIKRSMKTFTELSNENSALHEVYAHAV
LGHHPHVVRYYSSWAEDDHMIIQNEYCNGGSLQAAISENTKSGNHFEEPKLKD
ILLQISLGLNYIHNSSMVHLDIKPSNIFICHKMQSESSGVIEEVENEADWFLS
ANVMYKIGDLGHATSINKPKVEEGDSRFLANEILQEDYRHLPKADIFALGLTI
AVAAGAESLPTNGAAWHHIRKGNFPDVPQELSESFSSLLKNMIQPDAEQRPSA
AALARNTVLRPSLGKTEELQQQLNLEKFKTATLERELREAQQAQSPQGYTHHG
DTGVSGTHTGSRSTKRLVGGKSARSSSFTYTQILTMNYNGLRYSVQPHAVRFA
AWKQQATPQSRGVSRLHHLGRQSTFCGVRTATKSPNDAILRPYPVVKVLRQFV
RHESETTTSLVLERSLNRVHLLGRVGQDPVLRQVEGKNPVTIFSLATNEMWRS
GDSEVYQLGDVSQKTTWHRISVFRPGLRDVAYQYVKKGSRIYLEGKIDYGEYM
DKNNVRRQATTIIAGILSVTKKPPPVDGTLGFFHSDINSSSLF
```

Fig. 7

```
BLASTP - alignment of 276_protd against swissnew|P47817|WEE1_XENLA
WEE1-LIKE PROTEIN KINASE (EC 2.7.1.112). trembl|U13962|XL13962_1 gene: "Xe-Wee1A";
product: "Wee1A kinase"; Xenopus laevis Wee1A kinase (Xe-Wee1A) mRNA, complete cds.
This hit is scoring at : 5e-143 (expectation value)
Alignment length (overlap) : 531
Identities : 53 %
Scoring matrix : BLOSUM62 (used to infer consensus pattern)
Database searched : nrdb_1_;

Q:  38 SQTPXKGXVQDSXAKGTPPW--TPLSNVHXLDTSSXKDKXSPDQILRTPVSHPLKCPETP
       ::  P.KG.  .S  .:.  P:   TP .N ..L    S  .:.:SP..:...  S  .:CP TP
H:  31 NEGPQKGSPVSSWRTNNCPFPITPQRNEREL---SPTQELSPSSDYSPDPSVGAECPGTP

AQPDSRSKLLPSDSPSTPKTMLSRLVISPTGKLPSRGPKHLKLTPAPLKDEMTSLALVNI
       ..  .KL  .D:P TPK::L .:  SP .:: RG.: L:.. A  E:. :LVNI
       LHYSTWKKLKLCDTPYTPKSLLYKTLPSPGSRVHCRGQRLLRFV-AGTGAELDDPSLVNI

NPFTPESYKKLFLQSGGKRKIRGDLE-------EAGPEEGKGGLPAKRCVLRETNMASRY
       NPFTPESY:.:..Q..GKRK R .:   .  : .  .:E  .  . .:KR VLRETNM.SRY
       NPFTPESYRQTHFQPNGKRKERPEDDCRTDRQMKYAEKEHPAVFQSKRFVLRETNMGSRY

EKEFLEVEKIGVGEFGTVYKCIKRLDGCVYAIKRSMKTFTELSNENSALHEVYAHAVLGH
       :.EFLE:EKIG.GEFG:V:KC:KRLDGC.YAIKRS.K... :  :E. AL.EVYAHAVLGH
       KTEFLEIEKIGAGEFGSVFKCVKRLDGCFYAIKRSKKPLAGSTDEQLALREVYAHAVLGH
       The protein kinases ATP-binding region signature is underlined.
       The ATP-binding site "K" is shown in bold HPHVVRYYSSWAEDDHMIIQNEYCNGGSLQAAISENTKSGNHFEEPKLKDILLQISLGLN
       HPHVVRYYS:WAEDDHMIIQNEYCNGGSLQ .I :N.K.G.. E.:LK:ILLQ:S:GL.
       HPHVVRYYSAWAEDDHMIIQNEYCNGGSLQDLIVDNNKEGQFVLEQELKEILLQVSMGLK
```

Fig. 7 (continued)

```
YIHNSSMVHLDIKPSNIFIFICHKMQSESSGVIEEVENEADWFLSANVMYKIGDLGHATSIN
YIH.S.:VH:DIKPSNIFIC.K....       EE :.E D  .S.:V:YKIGDLGH.TSI
YIHGSLVHMDIKPSNIFICRKQTELGQ----EESDGEDD-LSSGSVLYKIGDLGHVTSIL
The WEE1-like serine/threonine protein kinase active-site signature
is underlined. The active site "D" is shown in bold KPKVEEGDSRFLANEILQEDYRHLPKADIFALGLTIAVAAGAESLPTNGAAWHHIRKGNF
.P:VEEGDSRFLANEILQEDY..LPKADIFALGLTIA.:AAGA..LP.N  :WHHIRKGN.
NPQVEEGDSRFLANEILQEDYSQLPKADIFALGLTIALAAGAAPLPCNEDSWHHIRKGNL PDVPQELSESFSSLLKNMIQPDAEQRPSAAALARNTVLRPSLGKTEELQQQLNLEKFKTA
P.VPQ L:. F :LLK ::.PD. .RP.AA:LA:N:VLR  .:GK. .:LQ:QLN:EKFKTA
PHVPQLLTPVFLALLKLLVHPDDPVMRPPAASLAKNSVLRRCVGKAAQLQKQLNVEKFKTA TLERELREAQQAQSPQGYTHHGDTGVSGTHTGSRSTKRLVGGKSARSSSFT       559
.LEREL:.A: AQ:. :. .:SG  .R. .KRLVG.K:.RS SFT
MLERELKAAKLAQTSGKDECSDLPPMSG--FSCRGRKRLVGAKNTRSLSFT       551
```

The eukaryotic protein kinase domain region identified by pfam-homology is from amino acids 212 to 480.

Fig. 8

HMMPFAM - alignment of 276_protd against pfam|hmm|pkinase
Eukaryotic protein kinase domain with high confidence (e-value of 6.4e-45)

```
This hit is scoring at : 162.7
Scoring matrix : BLOSUM62 (used to infer consensus pattern)
Q:  212 FLEVEKIGVGEFGTVYKCIKR1DGCVYAIKRSMKTFTElsnensaLHEVYAHAVLGhHPH
        :  :EK:G G.FG.VYK.:  .G  :.A:K  .K..      L.E::   L.  HP:
H:    1 yeleklGeGsfGkVykakhk.tgkivAvKilkkesls......lrEiqilkrls.HpN VVRYYSSWA-EDDHMIIQNEYCNGGSLQAAISENTksgnHFEEPKLKDILLQISLGLNYI
        :VR..:..DDH::.:  EY..GG.L  :..N      E.:.K.I.LQI   GL.Y:
        IvrligvfedtddhlylvmEymegGdLfdylrrng...plsekeakkialQilrGleYL HNSSMVHLDIKPSNIFICHKmqsessgvieeveneadwflsanVMYKIGDLGHATSINKP
        H:::.VH D:KP.NI.::                        .KI.D.G A.:.K
        HsngivHRDLKpeNILlden................gtvKiaDFGLArllekl KVEEGDSRFL-ANEI-LQEdYRHLPKADIFALGLTIAVAA-G---------------
        .G. .: A E: L:  : .K.D:::LG:::  G
        ttfvGTpwYmmAPEvileg.rgysskvDvWSlGviLyElitggplfpgadlpaftggdev ------AESLP----------TNGAAWHHIRKGnFPDVPQELSESFSSLLKNMIQPDAEQ
                                     I:K      :P...SE...LLK.:.D.:
        dqliifvlklPfsdelpktridpleelfrikkr.rlplpsncSeeikdLlkkcLnkDPsk RP---SAAAL       480
RP  :A..:
RpGsatakei       272
```

REGULATION OF HUMAN WEE1-LIKE SERINE/THREONINE PROTEIN KINASE

This application is a National Stage application of co-pending PCT application PCT/EP02/00912 filed Jan. 30, 2002, which was published in English under PCT Article 21(2) on Aug. 8, 2002, which claims the benefit of U.S. provisional application Ser. No. 60/265,352 filed Feb. 1, 2001, Ser. No. 60/324,051 filed Sep. 24, 2001, and Ser. No. 60/334,974 filed Dec. 4, 2001. These applications are incorporated herein by reference in their entireties.

TECHNICAL FIELD OF THE INVENTION

The invention relates to the regulation of human WEE1-like serine/threonine protein kinase.

BACKGROUND OF THE INVENTION

Protein tyrosine kinases catalyze the following reaction: ATP+protein tyrosine=ADP+protein tyrosine phosphate. Because of the importance of this reaction, there is a need in the art to identify protein kinases, which can be regulated to provide therapeutic effects.

SUMMARY OF THE INVENTION

It is an object of the invention to provide reagents and methods of regulating a human WEE1-like serine/threonine protein kinase. This and other objects of the invention are provided by one or more of the embodiments described below.

One embodiment of the invention is a WEE1-like serine/threonine protein kinase polypeptide comprising an amino acid sequence selected from the group consisting of:
amino acid sequences which are at least about 54% identical to the amino acid sequence shown in SEQ ID NO: 2;
the amino acid sequence shown in SEQ ID NO: 2;
amino acid sequences which are at least about 54% identical to the amino acid sequence shown in SEQ ID NO: 6; and
the amino acid sequence shown in SEQ ID NO: 6.

Yet another embodiment of the invention is a method of screening for agents which decrease extracellular matrix degradation. A test compound is contacted with a WEE1-like serine/threonine protein kinase polypeptide comprising an amino acid sequence selected from the group consisting of:
amino acid sequences which are at least about 54% identical to the amino acid sequence shown in SEQ ID NO: 2;
the amino acid sequence shown in SEQ ID NO: 2;
amino acid sequences which are at least about 54% identical to the amino acid sequence shown in SEQ ID NO: 6; and
the amino acid sequence shown in SEQ ID NO: 6.

Binding between the test compound and the WEE1-like serine/threonine protein kinase polypeptide is detected. A test compound which binds to the WEE1-like serine/threonine protein kinase polypeptide is thereby identified as a potential agent for decreasing extracellular matrix degradation. The agent can work by decreasing the activity of the WEE1-like serine/threonine protein kinase.

Another embodiment of the invention is a method of screening for agents which decrease extracellular matrix degradation. A test compound is contacted with a polynucleotide encoding a WEE1-like serine/threonine protein kinase polypeptide, wherein the polynucleotide comprises a nucleotide sequence selected from the group consisting of:
nucleotide sequences which are at least about 50% identical to the nucleotide sequence shown in SEQ ID NO: 1;
the nucleotide sequence shown in SEQ ID NO: 1;
nucleotide sequences which are at least about 50% identical to the nucleotide sequence shown in SEQ ID NO: 5; and
the nucleotide sequence shown in SEQ ID NO:5.

Binding of the test compound to the polynucleotide is detected. A test compound which binds to the polynucleotide is identified as a potential agent for decreasing extracellular matrix degradation. The agent can work by decreasing the amount of the WEE1-like serine/threonine protein kinase through interacting with the WEE1-like serine/threonine protein kinase mRNA.

Another embodiment of the invention is a method of screening for agents which regulate extracellular matrix degradation. A test compound is contacted with a WEE1-like serine/threonine protein kinase polypeptide comprising an amino acid sequence selected from the group consisting of:
amino acid sequences which are at least about 54% identical to the amino acid sequence shown in SEQ ID NO: 2;
the amino acid sequence shown in SEQ ID NO: 2;
amino acid sequences which are at least about 54% identical to the amino acid sequence shown in SEQ ID NO: 6; and
the amino acid sequence shown in SEQ ID NO: 6.

A WEE1-like serine/threonine protein kinase activity of the polypeptide is detected. A test compound which increases WEE1-like serine/threonine protein kinase activity of the polypeptide relative to WEE1-like serine/threonine protein kinase activity in the absence of the test compound is thereby identified as a potential agent for increasing extracellular matrix degradation. A test compound which decreases WEE1-like serine/threonine protein kinase activity of the polypeptide relative to WEE1-like serine/threonine protein kinase activity in the absence of the test compound is thereby identified as a potential agent for decreasing extracellular matrix degradation.

Even another embodiment of the invention is a method of screening for agents which decrease extracellular matrix degradation. A test compound is contacted with a WEE1-like serine/threonine protein kinase product of a polynucleotide which comprises a nucleotide sequence selected from the group consisting of:
nucleotide sequences which are at least about 50% identical to the nucleotide sequence shown in SEQ ID NO: 1;
the nucleotide sequence shown in SEQ ID NO: 1;
nucleotide sequences which are at least about 50% identical to the nucleotide sequence shown in SEQ ID NO: 5; and
the nucleotide sequence shown in SEQ ID NO:5.

Binding of the test compound to the WEE1-like serine/threonine protein kinase product is detected. A test compound which binds to the WEE1-like serine/threonine protein kinase product is thereby identified as a potential agent for decreasing extracellular matrix degradation.

Still another embodiment of the invention is a method of reducing extracellular matrix degradation. A cell is contacted with a reagent which specifically binds to a polynucleotide encoding a WEE1-like serine/threonine protein kinase polypeptide or the product encoded by the polynucleotide, wherein the polynucleotide comprises a nucleotide sequence selected from the group consisting of:
nucleotide sequences which are at least about 50% identical to the nucleotide sequence shown in SEQ ID NO: 1;
the nucleotide sequence shown in SEQ ID NO: 1;
nucleotide sequences which are at least about 50% identical to the nucleotide sequence shown in SEQ ID NO: 5; and
the nucleotide sequence shown in SEQ ID NO:5.

The invention thus provides a human WEE1-like serine/threonine protein kinase that can be used to identify test compounds that may act, for example, as activators or inhibitors at the enzyme's active site. Human WEE1-like serine/threonine protein kinase and fragments thereof also are useful in raising specific antibodies that can block the enzyme and effectively reduce its activity.

BRIEF DESCRIPTION OF THE DRAWINGS

FIG. 1 shows the DNA-sequence encoding a WEE1-like serine/threonine protein kinase Polypeptide (SEQ ID NO:1).

FIG. 2 shows the amino acid sequence deduced from the DNA-sequence of FIG. 1 (SEQ ID NO:2).

FIG. 3 shows the amino acid sequence of the protein identified by Swissnew Accession No. P47817|WEE1_XENLA WEE1-LIKE PROTEIN KINASE (EC 2.7.1.112) (SEQ ID NO:3).

FIG. 4 shows the DNA-sequence encoding a WEE1-like serine/threonine protein kinase Polypeptide (SEQ ID NO:4).

FIG. 5 shows the DNA-sequence encoding a WEE1-like serine/threonine protein kinase Polypeptide (SEQ ID NO:5).

FIG. 6 shows the amino acid sequence deduced from the DNA-sequence of FIG. 5 (SEQ ID NO:6).

FIG. 7 shows the BLASTP—alignment of 276_protd (SEQ ID NO:2) against swissnew|P47817|WEE1_XENLA WEE1-LIKE PROTEIN KINASE (EC 2.7.1.112) (SEQ ID NO:3).

FIG. 8 shows the HMMPFAM—alignment of 276_protd (SEQ ID NO:2) against pfam|hmm|pkinase.

DETAILED DESCRIPTION OF THE INVENTION

Figure 9:
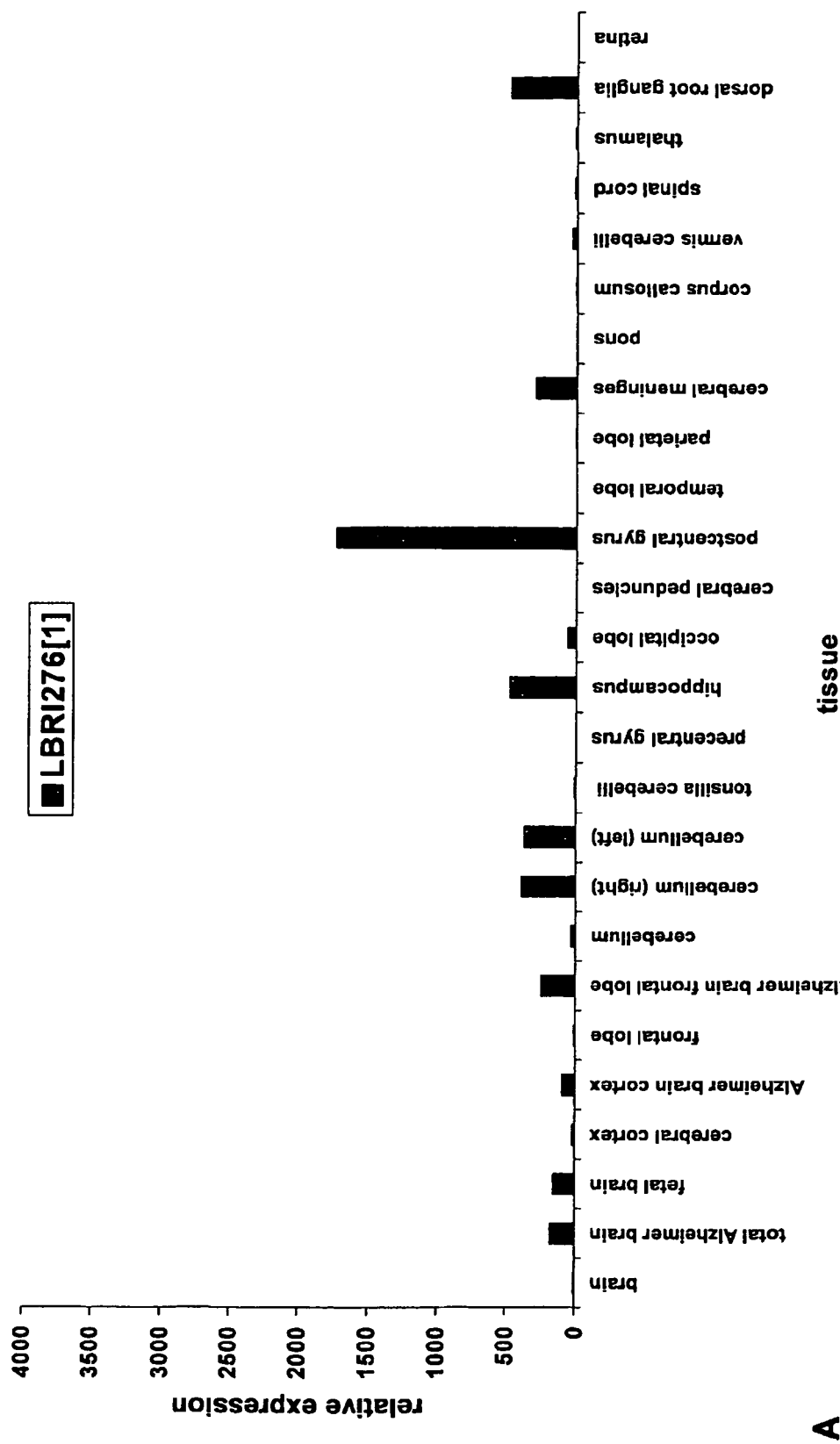
FIG. 9 shows the results of the WEE1-like protein kinase mRNA epression profiling in human tissues.

The invention relates to an isolated polynucleotide from the group consisting of:
a) a polynucleotide encoding a WEE1-like serine/threonine protein kinase polypeptide comprising an amino acid sequence selected from the group consisting of:
  amino acid sequences which are at least about 54% identical to the amino acid sequence shown in SEQ ID NO: 2;
  the amino acid sequence shown in SEQ ID NO: 2;
  amino acid sequences which are at least about 54% identical to the amino acid sequence shown in SEQ ID NO: 6; and
  the amino acid sequence shown in SEQ ID NO: 6.
b) a polynucleotide comprising the sequence of SEQ ID NOS: 1 or 5;
c) a polynucleotide which hybridizes under stringent conditions to a polynucleotide specified in (a) and (b) and encodes a WEE1-like serine/threonine protein kinase polypeptide;
d) a polynucleotide the sequence of which deviates from the polynucleotide sequences specified in (a) to (c) due to the degeneration of the genetic code and encodes a WEE1-like serine/threonine protein kinase polypeptide; and
e) a polynucleotide which represents a fragment, derivative or allelic variation of a polynucleotide sequence specified in (a) to (d) and encodes a WEE1-like serine/threonine protein kinase polypeptide.

Furthermore, it has been discovered by the present applicant that a novel WEE1-like serine/threonine protein kinase, particularly a human WEE1-like serine/threonine protein kinase can be used in therapeutic methods to treat cancer, a peripheral or central nervous system disorder, a genitourinary disorder, a cardiovascular disorder or COPD.

Human WEE1-like serine/threonine protein kinase comprises the amino acid sequence shown in SEQ ID NO:2 or 6. Coding sequences for SEQ ID NOS:2 and 6 shown in SEQ ID NOS:1 and 5, respectively. The WEE1-like serine/threonine protein kinase gene is located on chromosome 7. A related EST (SEQ ID NO:4) is expressed in pooled tissue comprising lung, testis, and B cells.

Human WEE1-like serine/threonine protein kinase is 53% identical over 531 amino acids to swissnew|P47817|WEE1_XENLA WEE1-LIKE PROTEIN KINASE (EC 2.7.1.112) (SEQ ID NO:3) with a confidence level of 5e-143. (FIG. 7). Human WEE1-like serine/threonine protein kinase also is 50% identical to a human "Wee1 Hu" protein, with a confidence level of 53–122. The function of SEQ ID NO:2 as a serine/threonine-specific eukaryotic protein kinase is supported by the presence of a eukaryotic protein kinase domain region identified by pfam homology (e-value of 6.4e-45), and a protein kinase ST and protein-kinase-ATP region identified by prosite homology.

The consensus pattern: [LIV]-G-{P}-G-{P}-[FYWMG-STNH]-[SGA]-{PW}-[LIVCAT]-{PD}-x-[GSTA-CLIVMFY]-x(5,18)-[LIVMFYWCSTAR]-[AIVP]-LIVM-FAGCKR]-K [K binds ATP] is present in SEQ ID NO:2. This pattern is present in the majority of known protein kinases, but fails to identify a number of them, especially viral kinases, which are quite divergent in this region and are completely missed by this pattern.

The consensus pattern: [LIVMFYC]-x-[HY]-x-D-[LIVMFY]-K-x(2)-N-[LIVMFYCT](3) [D is an active site residue] also is present in SEQ ID NO:2. This pattern detects most serine/threonine specific protein kinases, with 10 exceptions (half of them viral kinases) and also Epstein-Barr virus BGLF4 and *Drosophila* ninaC, which have, respectively, Ser and Arg instead of the conserved Lys and which are therefore detected by the tyrosine kinase specific pattern described below.

For proteins that have these two protein kinase signatures, the probability of being a protein kinase is close to 100%.

The consensus pattern: [LIVMFYC]-x-[HY]-x-D-[LIVMFY]-[RSTAC]-x(2)-N-[LIVMFYC](3) [D is an active site residue] is present all tyrosine specific protein kinases, with the exception of human ERBB3 and mouse blk. This pattern will also detect most bacterial aminoglycoside phosphotransferases and herpes-viruses ganciclovir kinases, which are proteins structurally and evolutionary related to protein kinases.

WEE1-like protein kinases have been shown to have a tyrosine-specific kinase activity. A sequence annotated as "similar to wee-like protein kinase" is present in the public database. Compared with this sequence, SEQ ID NO:2 contains an insertion of 18 amino acids that improves its identity to other wee-like protein kinases.

Human WEE1-like serine/threonine protein kinase of the invention is expected to be useful for the same purposes as previously identified WEE1-like serine/threonine protein kinase enzymes. Human WEE1-like serine/threonine protein kinase is believed to be useful in therapeutic methods to treat disorders such as cancer, peripheral and central nervous system disorders, genitourinary disorders, cardiovascular disorders, and COPD. Human WEE1-like serine/threonine protein kinase also can be used to screen for human WEE1-like serine/threonine protein kinase activators and inhibitors.

Polypeptides

Human WEE1-like serine/threonine protein kinase polypeptides according to the invention comprise at least 6, 10, 15, 20, 25, 50, 75, 100, 125, 150, 175, 200, 225, 250, 275, 300, 350, 400, 450, 500, 550, or 559 contiguous amino acids selected from the amino acid sequence shown in SEQ ID NO:2, at least 6, 10, 15, 20, 25, 50, 75, 100, 125, 150, 175, 200, 225, 250, 275, 300, 350, 400, 450, 500, 550, 600, 650, 700, 750, or 785 contiguous amino acids selected from the amino acid sequence shown in SEQ ID NO:6, or from biologically active variants thereof, as defined below. A WEE1-like serine/threonine protein kinase polypeptide of the invention therefore can be a portion of a WEE1-like serine/threonine protein kinase protein, a full-length WEE1-like serine/threonine protein kinase protein, or a fusion protein comprising all or a portion of a WEE1-like serine/threonine protein kinase protein.

Biologically Active Variants

Human WEE1-like serine/threonine protein kinase polypeptide variants which are biologically active, e.g., retain enzymatic activity, also are human WEE1-like serine/threonine protein kinase polypeptides. Preferably, naturally or non-naturally occurring human WEE1-like serine/threonine protein kinase polypeptide variants have amino acid sequences which are at least about 54, 55, 60, 65, or 70, preferably about 75, 80, 85, 90, 96, 96, 98, or 99% identical to the amino acid sequence shown in SEQ ID NO: 2 or 6. Percent identity between a putative human WEE1-like serine/threonine protein kinase polypeptide variant and an amino acid sequence of SEQ ID NO:2 is determined by conventional methods. See, for example, Altschul et al., *Bull. Math. Bio.* 48:603 (1986), and Henikoff & Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff & Henikoff, 1992.

Those skilled in the art appreciate that there are many established algorithms available to align two amino acid sequences. The "FASTA" similarity search algorithm of Pearson & Lipman is a suitable protein alignment method for examining the level of identity shared by an amino acid sequence disclosed herein and the amino acid sequence of a putative variant. The FASTA algorithm is described by Pearson & Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO: 2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman & Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of a human WEE1-like serine/threonine protein kinase polypeptide can be found using computer programs well known in the art, such as DNASTAR software.

The invention additionally, encompasses WEE1-like serine/threonine protein kinase polypeptides that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications can be carried out by known techniques including, but not limited, to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The WEE1-like serine/threonine protein kinase polypeptides may also be modified with a detectable label, such as an enzymatic, fluorescent, isotopic or affinity label to allow for detection and isolation of the protein.

The invention also provides chemically modified derivatives of WEE1-like serine/threonine protein kinase polypeptides that may provide additional advantages such as increased solubility, stability and circulating time of the polypeptide, or decreased immunogenicity (see U.S. Pat. No. 4,179,337). The chemical moieties for derivitization can be selected from water soluble polymers such as polyethylene glycol, ethylene glycol/propylene glycol copolymers, carboxymethylcellulose, dextran, polyvinyl alcohol, and the like. The polypeptides can be modified at random or predetermined positions within the molecule and can include one, two, three, or more attached chemical moieties.

Whether an amino acid change or a polypeptide modification results in a biologically active WEE1-like serine/ threonine protein kinase polypeptide can readily be determined by assaying for enzymatic activity, as described for example, in Nakanishi et al., Genes Cells 2000 October; 5(10): 839–47; Fattaey & Booher, Prog Cell Cycle Res 1997; 3:233–40; or Den Haese et al., Mol Biol Cell 1995 April; 6(4): 371–85.

Fusion Proteins

Fusion proteins are useful for generating antibodies against WEE1-like serine/threonine protein kinase polypeptide amino acid sequences and for use in various assay systems. For example, fusion proteins can be used to identify proteins that interact with portions of a WEE1-like serine/threonine protein kinase polypeptide. Protein affinity chromatography or library-based assays for protein-protein interactions, such as the yeast two-hybrid or phage display systems, can be used for this purpose. Such methods are well known in the art and also can be used as drug screens.

A WEE1-like serine/threonine protein kinase polypeptide fusion protein comprises two polypeptide segments fused together by means of a peptide bond. The first polypeptide segment comprises at least 6, 10, 15, 20, 25, 50, 75, 100, 125, 150, 175, 200, 225, 250, 275, 300, 350, 400, 450, 500, 550, or 559 contiguous amino acids selected from the amino acid sequence shown in SEQ ID NO:2, at least 6, 10, 15, 20, 25, 50, 75, 100, 125, 150, 175, 200, 225, 250, 275, 300, 350, 400, 450, 500, 550, 600, 650, 700, 750, or 785 contiguous amino acids selected from the amino acid sequence shown in SEQ ID NO:6, or from biologically active variants thereof, such as those described above. The first polypeptide segment also can comprise full-length WEE1-like serine/threonine protein kinase protein.

The second polypeptide segment can be a full-length protein or a protein fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the WEE1-like serine/threonine protein kinase polypeptide-encoding sequence and the heterologous protein sequence, so that the WEE1-like serine/threonine protein kinase polypeptide can be cleaved and purified away from the heterologous moiety.

A fusion protein can be synthesized chemically, as is known in the art. Preferably, a fusion protein is produced by covalently linking two polypeptide segments or by standard procedures in the art of molecular biology. Recombinant DNA methods can be used to prepare fusion proteins, for example, by making a DNA construct which comprises coding sequences selected from SEQ ID NO:1 in proper reading frame with nucleotides encoding the second polypeptide segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human WEE1-like serine/threonine protein kinase polypeptide can be obtained using WEE1-like serine/threonine protein kinase polypeptide polynucleotides (described below) to make suitable probes or primers for screening cDNA expression libraries from other species, such as mice, monkeys, or yeast, identifying cDNAs which encode homologs of WEE1-like serine/threonine protein kinase polypeptide, and expressing the cDNAs as is known in the art.

Polynucleotides

A WEE1-like serine/threonine protein kinase polynucleotide can be single- or double-stranded and comprises a coding sequence or the complement of a coding sequence for a WEE1-like serine/threonine protein kinase polypeptide. Degenerate nucleotide sequences encoding human WEE1-like serine/threonine protein kinase polypeptides, as well as homologous nucleotide sequences which are at least about 50, 55, 60, 65, 70, preferably about 75, 90, 96, 98, or 99% identical to the nucleotide sequence shown in SEQ ID NO:1 or 5 or their complements also are WEE1-like serine/threonine protein kinase polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of WEE1-like serine/threonine protein kinase polynucleotides that encode biologically active WEE1-like serine/threonine protein kinase polypeptides also are WEE1-like serine/threonine protein kinase polynucleotides. Polynucleotide fragments comprising at least 8, 9, 10, 11, 12, 15, 20, or 25 contiguous nucleotides of SEQ ID NO:1 or 5 or their complements also are WEE1-like serine/threonine protein kinase polynucleotides. These fragments can be used, for example, as hybridization probes or as antisense oligonucleotides.

Identification of Polynucleotide Variants and Homologs

Variants and homologs of the WEE1-like serine/threonine protein kinase polynucleotides described above also are WEE1-like serine/threonine protein kinase polynucleotides. Typically, homologous WEE1-like serine/threonine protein kinase polynucleotide sequences can be identified by hybridization of candidate polynucleotides to known WEE1-like serine/threonine protein kinase polynucleotides under stringent conditions, as is known in the art. For example, using the following wash conditions—2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the WEE1-like serine/threonine protein kinase polynucleotides disclosed herein also can be identified by making suitable probes or primers and screening cDNA expression libraries from other species, such as mice, monkeys, or yeast. Human variants of WEE1-like serine/threonine protein kinase polynucleotides can be identified, for example, by screening human cDNA expression libraries. It is well known that the $T_m$ of a double-stranded DNA decreases by 1–1.5° C. with every 1% decrease in homology (Bonner et al., *J. Mol. Biol.* 81, 123 (1973). Variants of human WEE1-like serine/threonine protein kinase polynucleotides or WEE1-like serine/threonine protein kinase polynucleotides of other species can therefore be identified by hybridizing a putative homologous WEE1-like serine/threonine protein kinase polynucleotide with a polynucleotide having a nucleotide sequence of SEQ ID NO:1 or 6 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to WEE1-like serine/threonine protein kinase polynucleotides or their complements following stringent hybridization and/or wash conditions also are WEE1-like serine/threonine protein kinase polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between a WEE1-like serine/threonine protein kinase polynucleotide having a nucleotide sequence shown in SEQ ID NO:1 or 6 or the complement thereof and a polynucleotide sequence which is at least about 50, preferably about 75, 90, 96, or 98% identical to one of those nucleotide sequences can be calculated, for example, using the equation of Bolton and McCarthy, *Proc. Natl. Acad. Sci. U.S.A.* 48, 1390 (1962): $T_m = 81.5° C. - 16.6(\log_{10}[Na^+]) + 0.41(\% G+C) - 0.63(\% \text{formamide}) - 600/l$, where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

A WEE1-like serine/threonine protein kinase polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated WEE1-like serine/threonine protein kinase polynucleotides. For example, restriction enzymes and probes can be used to isolate polynucleotide fragments, which comprise WEE1-like serine/threonine protein kinase nucleotide sequences. Isolated polynucleotides are in preparations that are free or at least 70, 80, or 90% free of other molecules.

Human WEE1-like serine/threonine protein kinase cDNA molecules can be made with standard molecular biology techniques, using WEE1-like serine/threonine protein kinase mRNA as a template. Human WEE1-like serine/threonine protein kinase cDNA molecules can thereafter be replicated using molecular biology techniques known in the art and disclosed in manuals such as Sambrook et al. (1989). An amplification technique, such as PCR, can be used to obtain additional copies of polynucleotides of the invention, using either human genomic DNA or cDNA as a template.

Alternatively, synthetic chemistry techniques can be used to synthesize WEE1-like serine/threonine protein kinase polynucleotides. The degeneracy of the genetic code allows alternate nucleotide sequences to be synthesized which will encode a WEE1-like serine/threonine protein kinase polypeptide having, for example, an amino acid sequence shown in SEQ ID NO:2 or 6 or a biologically active variant thereof.

Extending Polynucleotides

The partial sequences disclosed herein can be used to identify the corresponding full length gene from which they were derived. The partial sequences can be nick-translated or end-labeled with $^{32}P$ using polynucleotide kinase using labeling methods known to those with skill in the art (BASIC METHODS IN MOLECULAR BIOLOGY, Davis et al., eds., Elsevier Press, N.Y., 1986). A lambda library prepared from human tissue can be directly screened with the labeled sequences of interest or the library can be converted en masse to pBluescript (Stratagene Cloning Systems, La Jolla, Calif. 92037) to facilitate bacterial colony screening (see Sambrook et al., MOLECULAR CLONING: A LABORATORY MANUAL, Cold Spring Harbor Laboratory Press (1989, pg. 1.20).

Both methods are well known in the art. Briefly, filters with bacterial colonies containing the library in pBluescript or bacterial lawns containing lambda plaques are denatured, and the DNA is fixed to the filters. The filters are hybridized with the labeled probe using hybridization conditions described by Davis et al., 1986. The partial sequences, cloned into lambda or pBluescript, can be used as positive controls to assess background binding and to adjust the hybridization and washing stringencies necessary for accurate clone identification. The resulting autoradiograms are compared to duplicate plates of colonies or plaques; each exposed spot corresponds to a positive colony or plaque. The colonies or plaques are selected, expanded and the DNA is isolated from the colonies for further analysis and sequencing.

Positive cDNA clones are analyzed to determine the amount of additional sequence they contain using PCR with one primer from the partial sequence and the other primer from the vector. Clones with a larger vector-insert PCR product than the original partial sequence are analyzed by restriction digestion and DNA sequencing to determine whether they contain an insert of the same size or similar as the mRNA size determined from Northern blot Analysis.

Once one or more overlapping cDNA clones are identified, the complete sequence of the clones can be determined, for example after exonuclease III digestion (McCombie et al., *Methods* 3, 33–40, 1991). A series of deletion clones are generated, each of which is sequenced. The resulting overlapping sequences are assembled into a single contiguous sequence of high redundancy (usually three to five overlapping sequences at each nucleotide position), resulting in a highly accurate final sequence.

Various PCR-based methods can be used to extend the nucleic acid sequences disclosed herein to detect upstream sequences such as promoters and regulatory elements. For example, restriction-site PCR uses universal primers to retrieve unknown sequence adjacent to a known locus (Sarkar, *PCR Methods Applic.* 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., *PCR Methods Applic.* 1, 111–119, 1991). In this method, multiple restriction enzyme digestions and ligations also can be used to place an engineered double-stranded sequence into an unknown fragment of the DNA molecule before performing PCR.

Another method which can be used to retrieve unknown sequences is that of Parker et al., *Nucleic Acids Res.* 19, 3055–3060, 1991). Additionally, PCR, nested primers, and PROMOTERFINDER libraries (CLONTECH, Palo Alto, Calif.) can be used to walk genomic DNA (CLONTECH, Palo Alto, Calif.). This process avoids the need to screen libraries and is useful in finding intron/exon junctions.

When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) that are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA that might be present in limited amounts in a particular sample.

Obtaining Polypeptides

Human WEE1-like serine/threonine protein kinase polypeptides can be obtained, for example, by purification from human cells, by expression of WEE1-like serine/threonine protein kinase polynucleotides, or by direct chemical synthesis.

Protein Purification

Human WEE1-like serine/threonine protein kinase polypeptides can be purified from any cell that expresses the polypeptide, including host cells that have been transfected with WEE1-like serine/threonine protein kinase expression constructs. A purified WEE1-like serine/threonine protein kinase polypeptide is separated from other compounds that normally associate with the WEE1-like serine/threonine protein kinase polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified WEE1-like serine/threonine protein kinase polypeptides is at least 80% pure; preferably, the preparations are 90%, 95%, or 99% pure. Purity of the preparations can be assessed by any means known in the art, such as SDS-polyacrylamide gel electrophoresis.

Expression of Polynucleotides

To express a WEE1-like serine/threonine protein kinase polynucleotide, the polynucleotide can be inserted into an expression vector that contains the necessary elements for the transcription and translation of the inserted coding sequence. Methods that are well known to those skilled in the art can be used to construct expression vectors containing sequences encoding WEE1-like serine/threonine protein kinase polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a WEE1-like serine/threonine protein kinase polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUE-SCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a WEE1-like serine/threonine protein kinase polypeptide, vectors based on SV40 or EBV can be used with an appropriate selectable marker.

Bacterial and Yeast Expression Systems

In bacterial systems, a number of expression vectors can be selected depending upon the use intended for the WEE1- like serine/threonine protein kinase polypeptide. For example, when a large quantity of a WEE1-like serine/threonine protein kinase polypeptide is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene). In a BLUESCRIPT vector, a sequence encoding the WEE1-like serine/threonine protein kinase polypeptide can be ligated into the vector in frame with sequences for the amino-terminal Met and the subsequent 7 residues of β-galactosidase so that a hybrid protein is produced. pIN vectors (Van Heeke & Schuster, *J. Biol. Chem.* 264, 5503–5509, 1989) or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al. (1989) and Grant et al., *Methods Enzymol.* 153, 516–544, 1987.

Plant and Insect Expression Systems

If plant expression vectors are used, the expression of sequences encoding WEE1-like serine/threonine protein kinase polypeptides can be driven by any of a number of promoters. For example, viral promoters such as the 35S and 19S promoters of CaMV can be used alone or in combination with the omega leader sequence from TMV (Takamatsu, *EMBO J.* 6, 307–311, 1987). Alternatively, plant promoters such as the small subunit of RUBISCO or heat shock promoters can be used (Coruzzi et al., *EMBO J.* 3, 1671–1680, 1984; Broglie et al., *Science* 224, 838–843, 1984; Winter et al., *Results Probl. Cell Differ.* 17, 85–105, 1991). These constructs can be introduced into plant cells by direct DNA transformation or by pathogen-mediated transfection. Such techniques are described in a number of generally available reviews (e.g., Hobbs or Murray, in MCGRAW HILL YEARBOOK OF SCIENCE AND TECHNOLOGY, McGraw Hill, New York, N.Y., pp. 191–196, 1992).

An insect system also can be used to express a WEE1-like serine/threonine protein kinase polypeptide. For example, in one such system *Autographa californica* nuclear polyhedrosis virus (AcNPV) is used as a vector to express foreign genes in *Spodoptera frugiperda* cells or in *Trichoplusia* larvae. Sequences encoding WEE1-like serine/threonine protein kinase polypeptides can be cloned into a non-essential region of the virus, such as the polyhedrin gene, and placed under control of the polyhedrin promoter. Successful insertion of WEE1-like serine/threonine protein kinase polypeptides will render the polyhedrin gene inactive and produce recombinant virus lacking coat protein. The recombinant viruses can then be used to infect *S. frugiperda* cells or *Trichoplusia* larvae in which WEE1-like serine/threonine protein kinase polypeptides can be expressed (Engelhard et al., *Proc. Nat. Acad. Sci.* 91, 3224–3227, 1994).

Mammalian Expression Systems

A number of viral-based expression systems can be used to express WEE1-like serine/threonine protein kinase polypeptides in mammalian host cells. For example, if an adenovirus is used as an expression vector, sequences encoding WEE1-like serine/threonine protein kinase polypeptides can be ligated into an adenovirus transcription/translation complex comprising the late promoter and tripartite leader sequence. Insertion in a non-essential E1 or E3 region of the viral genome can be used to obtain a viable virus that is capable of expressing a WEE1-like serine/threonine protein kinase polypeptide in infected host cells (Logan & Shenk, *Proc. Natl. Acad. Sci.* 81, 3655–3659, 1984). If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding WEE1-like serine/threonine protein kinase polypeptides. Such signals include the ATG initiation codon and adjacent sequences. In cases where sequences encoding a WEE1-like serine/threonine protein kinase polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system which is used (see Scharf et al., *Results Probl. Cell Differ.* 20, 125–162, 1994).

Host Cells

A host cell strain can be chosen for its ability to modulate the expression of the inserted sequences or to process the expressed WEE1-like serine/threonine protein kinase polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells that have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express WEE1-like serine/threonine protein kinase polypeptides can be transformed using expression vectors which can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells which successfully express the introduced WEE1-like serine/threonine protein kinase sequences. Resistant clones of stably transformed cells can be proliferated using tissue culture techniques appropriate to the cell type. See, for example, ANIMAL CELL CULTURE, R. I. Freshney, ed., 1986.

Any number of selection systems can be used to recover transformed cell lines.

These include, but are not limited to, the herpes simplex virus thymidine kinase (Wigler et al., Cell 11, 223–32, 1977) and adenine phosphoribosyltransferase (Lowy et al., Cell 22, 817–23, 1980) genes which can be employed in tk− or aprt− cells, respectively. Also, antimetabolite, antibiotic, or herbicide resistance can be used as the basis for selection. For example, dhfr confers resistance to methotrexate (Wigler et al., Proc. Natl. Acad. Sci. 77, 3567–70, 1980), npt confers resistance to the aminoglycosides, neomycin and G-418 (Colbere-Garapin et al., J. Mol. Biol. 150, 1–14, 1981), and als and pat confer resistance to chlorsulfuron and phosphinotricin acetyltransferase, respectively (Murray, 1992, supra). Additional selectable genes have been described. For example, trpB allows cells to utilize indole in place of tryptophan, or hisD, which allows cells to utilize histinol in place of histidine (Hartman & Mulligan, Proc. Natl. Acad. Sci. 85, 8047–51, 1988). Visible markers such as anthocyanins, β-glucuronidase and its substrate GUS, and luciferase and its substrate luciferin, can be used to identify transformants and to quantify the amount of transient or stable protein expression attributable to a specific vector system (Rhodes et al., Methods Mol. Biol. 55, 121–131, 1995).

Detecting Expression

Although the presence of marker gene expression suggests that the WEE1-like serine/threonine protein kinase polynucleotide is also present, its presence and expression may need to be confirmed. For example, if a sequence encoding a WEE1-like serine/threonine protein kinase polypeptide is inserted within a marker gene sequence, transformed cells containing sequences that encode a WEE1-like serine/threonine protein kinase polypeptide can be identified by the absence of marker gene function. Alternatively, a marker gene can be placed in tandem with a sequence encoding a WEE1-like serine/threonine protein kinase polypeptide under the control of a single promoter. Expression of the marker gene in response to induction or selection usually indicates expression of the WEE1-like serine/threonine protein kinase polynucleotide.

Alternatively, host cells which contain a WEE1-like serine/threonine protein kinase polynucleotide and which express a WEE1-like serine/threonine protein kinase polypeptide can be identified by a variety of procedures known to those of skill in the art. These procedures include, but are not limited to, DNA-DNA or DNA-RNA hybridizations and protein bioassay or immunoassay techniques that include membrane, solution, or chip-based technologies for the detection and/or quantification of nucleic acid or protein. For example, the presence of a polynucleotide sequence encoding a WEE1-like serine/threonine protein kinase polypeptide can be detected by DNA-DNA or DNA-RNA hybridization or amplification using probes or fragments or fragments of polynucleotides encoding a WEE1-like serine/threonine protein kinase polypeptide. Nucleic acid amplification-based assays involve the use of oligonucleotides selected from sequences encoding a WEE1-like serine/threonine protein kinase polypeptide to detect transformants that contain a WEE1-like serine/threonine protein kinase polynucleotide.

A variety of protocols for detecting and measuring the expression of a WEE1-like serine/threonine protein kinase polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a WEE1-like serine/threonine protein kinase polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., J. Exp. Med. 158, 1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding WEE1-like serine/threonine protein kinase polypeptides include oligolabeling, nick translation, end-labeling, or PCR amplification using a labeled nucleotide. Alternatively, sequences encoding a WEE1-like serine/threonine protein kinase polypeptide can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with nucleotide sequences encoding a WEE1-like serine/threonine protein kinase polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode WEE1-like serine/threonine protein kinase polypeptides can be designed to contain signal sequences which direct secretion of soluble WEE1-like serine/threonine protein kinase polypeptides through a prokaryotic or eukaryotic cell membrane or which direct the membrane insertion of membrane-bound WEE1-like serine/threonine protein kinase polypeptide.

As discussed above, other constructions can be used to join a sequence encoding a WEE1-like serine/threonine protein kinase polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor Xa or enterokinase (Invitrogen, San Diego, Calif.) between the purification domain and the WEE1-like serine/threonine protein kinase polypeptide also can be used to facilitate purification. One such expression vector provides for expression of a fusion protein containing a WEE1-like serine/threonine protein kinase polypeptide and 6 histidine residues preceding a thioredoxin or an enterokinase cleavage site. The histidine residues facilitate purification by IMAC (immobilized metal ion affinity chromatography, as described in Porath et al., Prot. Exp. Purif. 3, 263–281, 1992), while the enterokinase cleavage site provides a means for purifying the WEE1-like serine/threonine protein kinase polypeptide from the fusion protein. Vectors that contain fusion proteins are disclosed in Kroll et al., DNA Cell Biol. 12, 441–453, 1993.

Chemical Synthesis

Sequences encoding a WEE1-like serine/threonine protein kinase polypeptide can be synthesized, in whole or in part, using chemical methods well known in the art (see Caruthers et al., Nucl. Acids Res. Symp. Ser. 215–223, 1980; Horn et al. Nucl. Acids Res. Symp. Ser. 225–232, 1980). Alternatively, a WEE1-like serine/threonine protein kinase polypeptide itself can be produced using chemical methods to synthesize its amino acid sequence, such as by direct peptide synthesis using solid-phase techniques (Merrifield, J. Am. Chem. Soc. 85, 2149–2154, 1963; Roberge et al., Science 269, 202–204, 1995). Protein synthesis can be performed using manual techniques or by automation. Automated synthesis can be achieved, for example, using Applied Biosystems 431A Peptide Synthesizer (Perkin Elmer). Optionally, fragments of WEE1-like serine/threonine protein kinase polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, WH Freeman and Co., New York, N.Y., 1983). The composition of a synthetic WEE1-like serine/threonine protein kinase polypeptide can be confirmed by amino acid analysis or sequencing (e.g., the Edman degradation procedure; see Creighton, supra). Additionally, any portion of the amino acid sequence of the WEE1-like serine/threonine protein kinase polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce WEE1-like serine/threonine protein kinase polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life that is longer than that of a transcript generated from the naturally occurring sequence.

The nucleotide sequences disclosed herein can be engineered using methods generally known in the art to alter WEE1-like serine/threonine protein kinase polypeptide-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of a WEE1-like serine/threonine protein kinase polypeptide. "Antibody" as used herein includes intact immunoglobulin molecules, as well as fragments thereof, such as Fab, $F(ab')_2$, and Fv, which are capable of binding an epitope of a WEE1-like serine/threonine protein kinase polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a WEE1-like serine/threonine protein kinase polypeptide can be used therapeutically, as well as in immuno chemical assays, such as Western blots, ELISAs, radioimmunoassays, immuno histochemical assays, immunoprecipitations, or other immunochemical assays known in the art. Various immunoassays can be used to identify antibodies having the desired specificity. Numerous protocols for competitive binding or immuno radiometric assays are well known in the art. Such immunoassays typically involve the measurement of complex formation between an immunogen and an antibody that specifically binds to the immunogen.

Typically, an antibody which specifically binds to a WEE1-like serine/threonine protein kinase polypeptide provides a detection signal at least 5-, 10-, or 20-fold higher than a detection signal provided with other proteins when used in an immunochemical assay. Preferably, antibodies which specifically bind to WEE1-like serine/threonine protein kinase polypeptides do not detect other proteins in immunochemical assays and can immunoprecipitate a WEE1-like serine/threonine protein kinase polypeptide from solution.

Human WEE1-like serine/threonine protein kinase polypeptides can be used to immunize a mammal, such as a mouse, rat, rabbit, guinea pig, monkey, or human, to produce polyclonal antibodies. If desired, a WEE1-like serine/threonine protein kinase polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies that specifically bind to a WEE1-like serine/threonine protein kinase polypeptide can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., Nature 256, 495–497, 1985; Kozbor et al., J. Immunol. Methods 81, 31–42, 1985; Cote et al., Proc. Natl. Acad. Sci. 80, 2026–2030, 1983; Cole et al., Mol. Cell Biol. 62, 109–120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 6851–6855, 1984; Neuberger et al., *Nature* 312, 604–608, 1984; Takeda et al., *Nature* 314, 452–454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, humanized antibodies can be produced using recombinant methods, as described in GB2188638B. Antibodies that specifically bind to a WEE1-like serine/threonine protein kinase polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies that specifically bind to WEE1-like serine/threonine protein kinase polypeptides. Antibodies with related specificity, but of distinct idiotypic composition, can be generated by chain shuffling from random combinatorial immunoglobin libraries (Burton, *Proc. Natl. Acad. Sci.* 88, 11120–23, 1991).

Single-chain antibodies also can be constructed using a DNA amplification method, such as PCR, using hybridoma cDNA as a template (Thirion et al., 1996, *Eur. J. Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., 1995, *Int. J. Cancer* 61, 497–501; Nicholls et al., 1993, *J. Immunol. Meth.* 165, 81–91).

Antibodies which specifically bind to WEE1-like serine/threonine protein kinase polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349, 293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which a WEE1-like serine/threonine protein kinase polypeptide is bound. The bound antibodies can then be eluted from the column using a buffer with a high salt concentration.

Antisense Olgonucleotides

Antisense oligonucleotides are nucleotide sequences that are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of WEE1-like serine/threonine protein kinase gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester intemucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583, 1990.

Modifications of WEE1-like serine/threonine protein kinase gene expression can be obtained by designing antisense oligonucleotides that will form duplexes to the control, 5', or regulatory regions of the WEE1-like serine/threonine protein kinase gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful complex formation between an antisense oligonucleotide and the complementary sequence of a WEE1-like serine/threonine protein kinase polynucleotide. Antisense oligonucleotides which comprise, for example, 2, 3, 4, or 5 or more stretches of contiguous nucleotides which are precisely complementary to a WEE1-like serine/threonine protein kinase polynucleotide, each separated by a stretch of contiguous nucleotides which are not complementary to adjacent WEE1-like serine/threonine protein kinase nucleotides, can provide sufficient targeting specificity for WEE1-like serine/threonine protein kinase mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular WEE1-like serine/threonine protein kinase polynucleotide sequence.

Antisense oligonucleotides can be modified without affecting their ability to hybridize to a WEE1-like serine/threonine protein kinase polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., *Trends Biotechnol.* 10, 152–158, 1992; Uhlmann et al., *Chem. Rev.* 90, 543–584, 1990; Uhlmann et al., *Tetrahedron. Lett.* 215, 3539–3542, 1987.

Ribozymes

Ribozymes are RNA molecules with catalytic activity. See, e.g., Cech, *Science* 236, 1532–1539; 1987; Cech, *Ann. Rev. Biochem.* 59, 543–568; 1990, Cech, *Curr. Opin. Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of a WEE1-like serine/threonine protein kinase polynucleotide can be used to generate ribozymes that will specifically bind to mRNA transcribed from the WEE1-like serine/threonine protein kinase polynucleotide. Methods of designing and constructing ribozymes which can cleave other RNA molecules in trans in a highly sequence specific manner have been developed and described in the art (see Haseloff et al. *Nature* 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a WEE1-like serine/threonine protein kinase RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate WEE1-like serine/threonine protein kinase RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease WEE1-like serine/threonine protein kinase expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors that induce expression of a target gene. Ribozymes also can be engineered to provide an additional level of regulation, so that destruction of mRNA occurs only when both a ribozyme and a target gene are induced in the cells.

Differentially Expressed Genes

Described herein are methods for the identification of genes whose products interact with human WEE1-like serine/threonine protein kinase. Such genes may represent genes that are differentially expressed in disorders including, but not limited to, cancer, peripheral and central nervous system disorders, genitourinary disorders, cardiovascular disorders, and COPD. Further, such genes may represent genes that are differentially regulated in response to manipulations relevant to the progression or treatment of such diseases. Additionally, such genes may have a temporally modulated expression, increased or decreased at different stages of tissue or organism development. A differentially expressed gene may also have its expression modulated under control versus experimental conditions. In addition, the human WEE1-like serine/threonine protein kinase gene or gene product may itself be tested for differential expression.

The degree to which expression differs in a normal versus a diseased state need only be large enough to be visualized via standard characterization techniques such as differential display techniques. Other such standard characterization techniques by which expression differences may be visualized include but are not limited to, quantitative RT (reverse transcriptase), PCR, and Northern analysis.

Identification of Differentially Expressed Genes

To identify differentially expressed genes total RNA or, preferably, mRNA is isolated from tissues of interest. For example, RNA samples are obtained from tissues of experimental subjects and from corresponding tissues of control subjects. Any RNA isolation technique that does not select against the isolation of mRNA may be utilized for the purification of such RNA samples. See, for example, Ausubel et al., ed., CURRENT PROTOCOLS IN MOLECULAR BIOLOGY, John Wiley & Sons, Inc. New York, 1987–1993. Large numbers of tissue samples may readily be processed using techniques well known to those of skill in the art, such as, for example, the single-step RNA isolation process of Chomczynski, U.S. Pat. No. 4,843,155.

Transcripts within the collected RNA samples that represent RNA produced by differentially expressed genes are identified by methods well known to those of skill in the art. They include, for example, differential screening (Tedder et al., *Proc. Natl. Acad. Sci. U.S.A.* 85, 208–12, 1988), subtractive hybridization (Hedrick et al., *Nature* 308, 149–53; Lee et al., *Proc. Natl. Acad. Sci. USA.* 88, 2825, 1984), and, preferably, differential display (Liang & Pardee, *Science* 257, 967–71, 1992; U.S. Pat. No. 5,262,311).

The differential expression information may itself suggest relevant methods for the treatment of disorders involving the human WEE1-like serine/threonine protein kinase. For example, treatment may include a modulation of expression of the differentially expressed genes and/or the gene encoding the human WEE1-like serine/threonine protein kinase. The differential expression information may indicate whether the expression or activity of the differentially expressed gene or gene product or the human WEE1-like serine/threonine protein kinase gene or gene product are up-regulated or down-regulated.

Screening Methods

The invention provides assays for screening test compounds that bind to or modulate the activity of a WEE1-like serine/threonine protein kinase polypeptide or a WEE1-like serine/threonine protein kinase polynucleotide. A test compound preferably binds to a WEE1-like serine/threonine protein kinase polypeptide or polynucleotide. More preferably, a test compound decreases or increases WEE1-like serine/threonine protein kinase activity by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.* 12, 145, 1997.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994). Libraries of compounds can be presented in solution (see, e.g., Houghten, *BioTechniques* 13, 412–421, 1992), or on beads (Lam, *Nature* 354, 82–84, 1991), chips (Fodor, *Nature* 364, 555–556, 1993), bacteria or spores (Ladner, U.S. Pat. No. 5,223,409), plasmids (Cull et al., *Proc. Natl. Acad. Sci. U.S.A.* 89, 1865–1869, 1992), or phage (Scott & Smith, *Science* 249, 386–390, 1990; Devlin, *Science* 249, 404–406, 1990); Cwirla el al., *Proc. Natl. Acad. Sci.* 97, 6378–6382, 1990; Felici, *J. Mol. Biol.* 222, 301–310, 1991; and Ladner, U.S. Pat. No. 5,223,409).

High Throughput Screening

Test compounds can be screened for the ability to bind to WEE1-like serine/threonine protein kinase polypeptides or polynucleotides or to affect WEE1-like serine/threonine protein kinase activity or WEE1-like serine/threonine protein kinase gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 μl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad. Sci. U.S.A.* 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule that binds to and occupies, for example, the active site of the WEE1-like serine/threonine protein kinase polypeptide, such that normal biological activity is prevented. Examples of such small molecules include, but are not limited to, small peptides or peptide-like molecules.

In binding assays, either the test compound or the WEE1-like serine/threonine protein kinase polypeptide can comprise a detectable label, such as a fluorescent, radioisotopic, chemiluminescent, or enzymatic label, such as horseradish peroxidase, alkaline phosphatase, or luciferase. Detection of a test compound that is bound to the WEE1-like serine/threonine protein kinase polypeptide can then be accomplished, for example, by direct counting of radioemission, by scintillation counting, or by determining conversion of an appropriate substrate to a detectable product.

Alternatively, binding of a test compound to a WEE1-like serine/threonine protein kinase polypeptide can be determined without labeling either of the interactants. For example, a microphysiometer can be used to detect binding of a test compound with a WEE1-like serine/threonine protein kinase polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a WEE1-like serine/threonine protein kinase polypeptide (McConnell et al., Science 257, 1906–1912, 1992).

Determining the ability of a test compound to bind to a WEE1-like serine/threonine protein kinase polypeptide also can be accomplished using a technology such as real-time Bimolecular Interaction Analysis (BIA) (Sjolander & Urbaniczky, Anal. Chem. 63, 2338–2345, 1991, and Szabo et al., Curr. Opin. Struct. Biol. 5, 699–705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a WEE1-like serine/threonine protein kinase polypeptide can be used as a "bait protein" in a two-hybrid assay or three-hybrid assay (see, e.g., U.S. Pat. No. 5,283,317; Zervos et al., Cell 72, 223–232, 1993; Madura et al., J. Biol. Chem. 268, 12046–12054, 1993; Bartel et al., BioTechniques 14, 920–924, 1993; Iwabuchi et al., Oncogene 8, 1693–1696, 1993; and Brent WO94/10300), to identify other proteins which bind to or interact with the WEE1-like serine/threonine protein kinase polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding a WEE1-like serine/threonine protein kinase polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein that interacts with the WEE1-like serine/threonine protein kinase polypeptide.

It may be desirable to immobilize either the WEE1-like serine/threonine protein kinase polypeptide (or polynucleotide) or the test compound to facilitate separation of bound from unbound forms of one or both of the interactants, as well as to accommodate automation of the assay. Thus, either the WEE1-like serine/threonine protein kinase polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the enzyme polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a WEE1-like serine/threonine protein kinase polypeptide (or polynucleotide) can be accomplished in any vessel suitable for containing the reactants. Examples of such vessels include microtiter plates, test tubes, and microcentrifuge tubes.

In one embodiment, the WEE1-like serine/threonine protein kinase polypeptide is a fusion protein comprising a domain that allows the WEE1-like serine/threonine protein kinase polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed WEE1-like serine/threonine protein kinase polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a WEE1-like serine/threonine protein kinase polypeptide (or polynucleotide) or a test compound can be immobilized utilizing conjugation of biotin and streptavidin. Biotinylated WEE1-like serine/threonine protein kinase polypeptides (or polynucleotides) or test compounds can be prepared from biotin-NHS(N-hydroxy-succinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a WEE1-like serine/threonine protein kinase polypeptide, polynucleotide, or a test compound, but which do not interfere with a desired binding site, such as the active site of the WEE1-like serine/threonine protein kinase polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the WEE1-like serine/threonine protein kinase polypeptide or test compound, enzyme-linked assays which rely on detecting an activity of the WEE1-like serine/threonine protein kinase polypeptide, and SDS gel electrophoresis under non-reducing conditions.

Screening for test compounds which bind to a WEE1-like serine/threonine protein kinase polypeptide or polynucleotide also can be carried out in an intact cell. Any cell which comprises a WEE1-like serine/threonine protein kinase polypeptide or polynucleotide can be used in a cell-based assay system. A WEE1-like serine/threonine protein kinase polynucleotide can be naturally occurring in the cell or can be introduced using techniques such as those described above. Binding of the test compound to a WEE1-like serine/threonine protein kinase polypeptide or polynucleotide is determined as described above.

Enzyme Assays

Test compounds can be tested for the ability to increase or decrease the WEE1-like serine/threonine protein kinase activity of a human WEE1-like serine/threonine protein kinase polypeptide. WEE1-like serine/threonine protein kinase activity can be measured, for example, as described in Nakanishi et al., Genes Cells 2000 October; 5(10): 839–47; Fattaey & Booher, Prog Cell Cycle Res 1997; 3:233–40; or Den Haese et al., Mol Biol Cell 1995 April; 6(4): 371–85.

Enzyme assays can be carried out after contacting either a purified WEE1-like serine/threonine protein kinase polypeptide, a cell membrane preparation, or an intact cell with a test compound. A test compound that decreases a WEE1-like serine/threonine protein kinase activity of a WEE1-like serine/threonine protein kinase polypeptide by at least about 10, preferably about 50, more preferably about 75, 90, or 100% is identified as a potential therapeutic agent for decreasing WEE1-like serine/threonine protein kinase activity. A test compound which increases a WEE1-like serine/threonine protein kinase activity of a human WEE1-like serine/threonine protein kinase polypeptide by at least about 10, preferably about 50, more preferably about 75, 90, or 100% is identified as a potential therapeutic agent for increasing human WEE1-like serine/threonine protein kinase activity.

Gene Expression

In another embodiment, test compounds that increase or decrease WEE1-like serine/threonine protein kinase gene expression are identified. A WEE1-like serine/threonine protein kinase polynucleotide is contacted with a test compound, and the expression of an RNA or polypeptide product of the WEE1-like serine/threonine protein kinase polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of WEE1-like serine/threonine protein kinase mRNA or polypeptide expression in the cells can be determined by methods well known in the art for detecting mRNA or polypeptide. Either qualitative or quantitative methods can be used. The presence of polypeptide products of a WEE1-like serine/threonine protein kinase polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a WEE1-like serine/threonine protein kinase polypeptide.

Such screening can be carried out either in a cell-free assay system or in an intact cell. Any cell that expresses a WEE1-like serine/threonine protein kinase polynucleotide can be used in a cell-based assay system. The WEE1-like serine/threonine protein kinase polynucleotide can be naturally occurring in the cell or can be introduced using techniques such as those described above. Either a primary culture or an established cell line, such as CHO or human embryonic kidney 293 cells, can be used.

Pharmaceutical Compositions

The invention also provides pharmaceutical compositions that can be administered to a patient to achieve a therapeutic effect. Pharmaceutical compositions of the invention can comprise, for example, a WEE1-like serine/threonine protein kinase polypeptide, WEE1-like serine/threonine protein kinase polynucleotide, ribozymes or antisense oligonucleotides, antibodies which specifically bind to a WEE1-like serine/threonine protein kinase polypeptide, or mimetics, activators, or inhibitors of a WEE1-like serine/threonine protein kinase polypeptide activity. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, ie., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents that increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%-2% sucrose, and 2–7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa). After pharmaceutical compositions have been prepared, they can be placed in an appropriate container and labeled for treatment of an indicated condition. Such labeling would include amount, frequency, and method of administration.

Therapeutic Indications and Methods

Human WEE1-like serine/threonine protein kinase can be regulated to treat cancer, peripheral and central nervous system disorders, genitourinary disorders, cardiovascular disorders, and COPD.

Cancer

Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard cancer therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Agonists and/or antagonists of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

COPD

Chronic obstructive pulmonary (or airways) disease (COPD) is a condition defined physiologically as airflow obstruction that generally results from a mixture of emphysema and peripheral airway obstruction due to chronic bronchitis (Senior & Shapiro, *Pulmonary Diseases and Disorders*, 3d ed., New York, McGraw-Hill, 1998, pp. 659–681, 1998; Barnes, *Chest* 117, 10S–14S, 2000). Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does occur in non-smokers.

Chronic inflammation of the airways is a key pathological feature of COPD (Senior & Shapiro, 1998). The inflammatory cell population comprises increased numbers of macrophages, neutrophils, and $CD8^+$ lymphocytes. Inhaled irritants, such as cigarette smoke, activate macrophages which are resident in the respiratory tract, as well as epithelial cells leading to release of chemokines (e.g., interleukin-8) and other chemotactic factors. These chemotactic factors act to increase the neutrophil/monocyte trafficking from the blood into the lung tissue and airways. Neutrophils and monocytes recruited into the airways can release a variety of potentially damaging mediators such as proteolytic enzymes and reactive oxygen species. Matrix degradation and emphysema, along with airway wall thickening, surfactant dysfunction, and mucus hypersecretion, all are potential sequelae of this inflammatory response that lead to impaired airflow and gas exchange.

Peripheral and Central Nervous System Disorders

Peripheral and central nervous system disorders which may be treated include brain injuries, cerebrovascular diseases and their consequences, Parkinson's disease, corticobasal degeneration, motor neuron disease, dementia, including ALS, multiple sclerosis, traumatic brain injury, stroke, post-stroke, post-traumatic brain injury, and small-vessel cerebrovascular disease. Dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld-Jakob dementia, HIV dementia, schizophrenia with dementia, and Korsakoff's psychosis also can be treated. Similarly, it may be possible to treat cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities, by regulating the activity of human WEE1-like serine/threonine protein kinase.

Pain that is associated with peripheral and central nervous system disorders also can be treated by regulating the activity of human WEE1-like serine/threonine protein kinase. Pain which can be treated includes that associated with central nervous system disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, cranial neuralgias, and post-herpetic neuralgia. Pain associated with cancer and cancer treatment also can be treated, as can headache pain (for example, migraine with aura, migraine without aura, and other migraine disorders), episodic and chronic tension-type headache, tension-type like headache, cluster headache, and chronic paroxysmal hemicrania.

Cardiovascular Disorders

Cardiovascular diseases include the following disorders of the heart and the vascular system: congestive heart failure, myocardial infarction, ischemic diseases of the heart, all kinds of atrial and ventricular arrhythmias, hypertensive vascular diseases, and peripheral vascular diseases.

Heart failure is defined as a pathophysiologic state in which an abnormality of cardiac function is responsible for the failure of the heart to pump blood at a rate commensurate with the requirement of the metabolizing tissue. It includes all forms of pumping failure, such as high-output and low-output, acute and chronic, right-sided or left-sided, systolic or diastolic, independent of the underlying cause.

Myocardial infarction (MI) is generally caused by an abrupt decrease in coronary blood flow that follows a thrombotic occlusion of a coronary artery previously narrowed by arteriosclerosis. MI prophylaxis (primary and secondary prevention) is included, as well as the acute treatment of MI and the prevention of complications.

Ischemic diseases are conditions in which the coronary flow is restricted resulting in a perfusion which inadequate to meet the myocardial requirement for oxygen. This group of diseases includes stable angina, unstable angina, and asymptomatic ischemia.

Arrhythmias include all forms of atrial and ventricular tachyarrhythmias (atrial tachycardia, atrial flutter, atrial fibrillation, atrio-ventricular reentrant tachycardia, preexcitation syndrome, ventricular tachycardia, ventricular flutter, and ventricular fibrillation), as well as bradycardic forms of arrhythmias.

Vascular diseases include primary as well as all kinds of secondary arterial hypertension (renal, endocrine, neurogenic, others). The disclosed gene and its product may be used as drug targets for the treatment of hypertension as well as for the prevention of all complications. Peripheral vascular diseases are defined as vascular diseases in which arterial and/or venous flow is reduced resulting in an imbalance between blood supply and tissue oxygen demand. It includes chronic peripheral arterial occlusive disease (PAOD), acute arterial thrombosis and embolism, inflammatory vascular disorders, Raynaud's phenomenon, and venous disorders.

Genitourinary Disorders

Urinary Incontinence.

Urinary incontinence (UI) is the involuntary loss of urine. Urge urinary incontinence (UUI) is one of the most common types of UI together with stress urinary incontinence (SUI), which is usually caused by a defect in the urethral closure mechanism. UUI is often associated with neurological disorders or diseases causing neuronal damage, such as dementia, Parkinson's disease, multiple sclerosis, stroke, and diabetes, although it also occurs in individuals with no such disorders. One of the usual causes of UUI is overactive bladder (OAB), which is a medical condition referring to the symptoms of frequency and urgency derived from abnormal contractions and instability of the detrusor muscle.

There are several medications for urinary incontinence on the market today, mainly to help treating UUI. Therapy for OAB is focused on drugs that affect peripheral neural control mechanisms or those that act directly on bladder detrusor smooth muscle contraction, with a major emphasis on development of anticholinergic agents. These agents can inhibit the parasympathetic nerves, which control bladder voiding, or can exert a direct spasmolytic effect on the detrusor muscle of the bladder. This results in a decrease in intravesicular pressure, an increase in capacity, and a reduction in the frequency of bladder contraction. Orally active anticholinergic drugs, such as propantheline (ProBanthine), tolterodine tartrate (Detrol), and oxybutynin (Ditropan), are the most commonly prescribed drugs. However, their most serious drawbacks are unacceptable side effects, such as dry mouth, abnormal visions, constipation, and central nervous system disturbances. These side effects lead to poor compliance. Dry mouth symptoms alone are responsible for a 70% non-compliance rate with oxybutynin. The inadequacies of present therapies highlight the need for novel, efficacious, safe, orally available drugs that have fewer side effects.

Benign Prostatic Hyperplasia.

Benign prostatic hyperplasia (BPH) is the benign nodular hyperplasia of the periurethral prostate gland commonly seen in men over the age of 50. The overgrowth occurs in the central area of the prostate called the transition zone, which wraps around the urethra. BPH causes variable degrees of bladder outlet obstruction, resulting in progressive lower urinary tract syndromes (LUTS) characterized by urinary frequency, urgency, and nocturia due to incomplete emptying and rapid refilling of the bladder. The actual cause of BPH is unknown but may involve age-related alterations in balance of steroidal sex hormones.

Selective α1-adrenoceptor antagonists, such as prazosin, indoramin, and tamsulosin, are used as an adjunct in the symptomatic treatment of urinary obstruction caused by BPH, although they do not affect on the underlying cause of BPH. In BPH, increased sympathetic tone exacerbates the degree of obstruction of the urethra through contraction of prostatic and urethral smooth muscle. These compounds inhibit sympathetic activity, thereby relaxing the smooth muscle of the urinary tract. Uroselective α1-antagonists and α1-antagonists with high tissue selectivity for lower urinary tract smooth muscle that do not provoke hypotensive side-effects should be developed for the treatment.

Drugs blocking dihydrotestosterone have been used to reduce the size of the prostate. 5α-reductase inhibitors such as finasteride are prescribed for BPH. These agents selectively inhibit 5α-reductase which mediates conversion of testosterone to dihydrotestosterone, thereby reducing plasma dihydrotestosterone levels and, thus, prostate growth. The 5α-reductase inhibitors do not bind to androgen receptors and do not affect testosterone levels, nor do they possess feminizing side-effects.

Androgen receptor antagonists are used for the treatment of prostatic hyperplasia due to excessive action or production of testosterone. Various antiandrogens are under investigation for BPH including chlormadione derivatives with no estrogenic activity, orally-active aromatase inhibitors, and luteinizing hormone-releasing hormone (LHRH) analogues.

This invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or a WEE1-like serine/threonine protein kinase polypeptide binding molecule) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects WEE1-like serine/threonine protein kinase activity can be administered to a human cell, either in vitro or in vivo, to reduce WEE1-like serine/threonine protein kinase activity. The reagent preferably binds to an expression product of a human WEE1-like serine/threonine protein kinase gene. If the expression product is a protein, the reagent is preferably an antibody. For treatment of human cells ex vivo, an antibody can be added to a preparation of stem cells that have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 μg of DNA per 16 nmole of liposome delivered to about $10^6$ cells, more preferably about 1.0 μg of DNA per 16 nmole of liposome delivered to about $10^6$ cells, and even more preferably about 2.0 μg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods that are standard in the art (see, for example, U.S. Pat. No. 5,705,151). Preferably, from about 0.1 μg to about 10 μg of polynucleotide is combined with about 8 nmol of liposomes, more preferably from about 0.5 μg to about 5 μg of polynucleotides are combined with about 8 nmol liposomes, and even more preferably about 1.0 μg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202–05 (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24 (1988); Wu et al., *J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991)

Determination of a Therapeutically Effective Dose

The determination of a therapeutically effective dose is well within the capability of those skilled in the art. A therapeutically effective dose refers to that amount of active ingredient which increases or decreases WEE1-like serine/threonine protein kinase activity relative to the WEE1-like serine/threonine protein kinase activity which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides that express antisense oligonucleotides or ribozymes can be introduced into cells by a variety of methods, as described above.

Preferably, a reagent reduces expression of a WEE1-like serine/threonine protein kinase gene or the activity of a WEE1-like serine/threonine protein kinase polypeptide by at least about 10, preferably about 50, more preferably about 75, 90, or 100% relative to the absence of the reagent. The effectiveness of the mechanism chosen to decrease the level of expression of a WEE1-like serine/threonine protein kinase gene or the activity of a WEE1-like serine/threonine protein kinase polypeptide can be assessed using methods well known in the art, such as hybridization of nucleotide probes to WEE1-like serine/threonine protein kinase-specific mRNA, quantitative RT-PCR, immunologic detection of a WEE1-like serine/threonine protein kinase polypeptide, or measurement of WEE1-like serine/threonine protein kinase activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

Diagnostic Methods

Human WEE1-like serine/threonine protein kinase also can be used in diagnostic assays for detecting diseases and abnormalities or susceptibility to diseases and abnormalities related to the presence of mutations in the nucleic acid sequences that encode the enzyme. For example, differences can be determined between the cDNA or genomic sequence encoding WEE1-like serine/threonine protein kinase in individuals afflicted with a disease and in normal individuals. If a mutation is observed in some or all of the afflicted individuals but not in normal individuals, then the mutation is likely to be the causative agent of the disease.

Sequence differences between a reference gene and a gene having mutations can be revealed by the direct DNA sequencing method. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR. The sequence determination is performed by conventional procedures using radiolabeled nucleotides or by automatic sequencing procedures using fluorescent tags.

Genetic testing based on DNA sequence differences can be carried out by detection of alteration in electrophoretic mobility of DNA fragments in gels with or without denaturing agents. Small sequence deletions and insertions can be visualized, for example, by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., Science 230, 1242, 1985). Sequence changes at specific locations can also be revealed by nuclease protection assays, such as RNase and S 1 protection or the chemical cleavage method (e.g., Cotton et al., Proc. Natl. Acad. Sci. USA 85, 4397–4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of WEE1-like serine/threonine protein kinase also can be detected in various tissues. Assays used to detect levels of the receptor polypeptides in a body sample, such as blood or a tissue biopsy, derived from a host are well known to those of skill in the art and include radioimmunoassays, competitive binding assays, Western blot analysis, and ELISA assays.

All patents, patent applications, and references cited in this disclosure are expressly incorporated herein by reference in their entireties. The above disclosure generally describes the present invention. A more complete understanding can be obtained by reference to the following specific examples, which are provided for purposes of illustration only and are not intended to limit the scope of the invention.

EXAMPLE 1

Detection of Serine-threonine Protein Kinase Activity

For high level expression of a FLAG-tagged serine-threonine protein kinase polypeptide, COS-1 cells are transfected with the expression vector serine-threonine protein kinase polypeptide (expressing the DNA-sequence of ID NO: 1) using the calcium phosphate method. After 5 h, the cells are infected with recombinant vaccinia virus vTF7-3 (10 plaque-forming units/cell). The cells are harvested 20 h after infection and lysed in 50 mM Tris, pH 7.5, 5 mM MgCl2, 0,1% Nonidet P-40, 0.5 mM dithiothreitol, 1 mM phenylmethylsulfonyl fluoride, 10 μg/ml aprotinin. Serine-threonine protein kinase polypeptide is immunoprecipitated from the lysate using anti-FLAG antibodies. In vitro kinase assay and phosphoamino acid analysis are performed in a volume of 40 μl with immunoprecipitated FLAG-serine-threonine protein kinase polypeptide in 50 mM Tris-HCl, pH 8.0, 50 mM NaCl, 5 mM MgCl2, 1 mM dithiothreitol. The reaction is started by the addition of 4 μl of 1 mM ATP supplemented with 5 μCi of (−32P)ATP and incubated for 30 min at 37° C. Afterward, the samples are subjected to SDS-PAGE and phosphorylated proteins are detected by autoradiography. Histone type III-S, casein, bovine serum albumin, or myelin basic proteins are used as substrates. It is shown that the polypeptide with the amino acid sequence of SEQ ID NO.: 2 has serine-threonine protein kinase activity.

EXAMPLE 2

Expression of Recombinant Human WEE1-like Serine/Threonine Protein Kinase

The *Pichia pastoris* expression vector pPICZB (Invitrogen, San Diego, Calif.) is used to produce large quantities of recombinant human WEE1-like serine/threonine protein kinase polypeptides in yeast. The WEE1-like serine/threonine protein kinase-encoding DNA sequence is derived from SEQ ID NO:1. Before insertion into vector pPICZB, the DNA sequence is modified by well known methods in such a way that it contains at its 5'-end an initiation codon and at its 3'-end an enterokinase cleavage site, a His6 reporter tag and a termination codon. Moreover, at both termini recognition sequences for restriction endonucleases are added and after digestion of the multiple cloning site of pPICZ B with the corresponding restriction enzymes the modified DNA sequence is ligated into pPICZB. This expression vector is designed for inducible expression in *Pichia pastoris*, driven by a yeast promoter. The resulting pPICZ/md-His6 vector is used to transform the yeast.

The yeast is cultivated under usual conditions in 5 liter shake flasks and the recombinantly produced protein isolated from the culture by affinity chromatography (Ni-NTA-Resin) in the presence of 8 M urea. The bound polypeptide is eluted with buffer, pH 3.5, and neutralized. Separation of the polypeptide from the His6 reporter tag is accomplished by site-specific proteolysis using enterokinase (Invitrogen, San Diego, Calif.) according to manufacturer's instructions. Purified human WEE1-like serine/threonine protein kinase polypeptide is obtained.

EXAMPLE 3

Identification of Test Compounds that Bind to WEE1-like Serine/Threonine Protein Kinase Polypeptides Purified WEE1-like serine/threonine protein kinase polypeptides comprising a glutathione-S-transferase protein and absorbed onto glutathione-derivatized wells of 96-well microtiter plates are contacted with test compounds from a small molecule library at pH 7.0 in a physiological buffer solution. Human WEE1-like serine/threonine protein kinase polypeptides comprise the amino acid sequence shown in SEQ ID NO:2. The test compounds comprise a fluorescent tag. The samples are incubated for 5 minutes to one hour. Control samples are incubated in the absence of a test compound.

The buffer solution containing the test compounds is washed from the wells. Binding of a test compound to a WEE1-like serine/threonine protein kinase polypeptide is detected by fluorescence measurements of the contents of the wells. A test compound that increases the fluorescence in a well by at least 15% relative to fluorescence of a well in which a test compound is not incubated is identified as a compound which binds to a WEE1-like serine/threonine protein kinase polypeptide.

EXAMPLE 4

Identification of a Test Compound which Decreases WEE1-like Serine/Threonine Protein Kinase Gene Expression A test compound is administered to a culture of human cells transfected with a WEE1-like serine/threonine protein kinase expression construct and incubated at 37° C. for 10 to 45 minutes. A culture of the same type of cells that have not been transfected is incubated for the same time without the test compound to provide a negative control.

RNA is isolated from the two cultures as described in Chirgwin et al., *Biochem.* 18, 5294–99, 1979). Northern blots are prepared using 20 to 30 μg total RNA and hybridized with a $^{32}$P-labeled WEE1-like serine/threonine protein kinase-specific probe at 65° C. in Express-hyb (CLONTECH). The probe comprises at least 11 contiguous nucleotides selected from the complement of SEQ ID NO:1. A test compound that decreases the WEE1-like serine/threonine protein kinase-specific signal relative to the signal obtained in the absence of the test compound is identified as an inhibitor of WEE1-like serine/threonine protein kinase gene expression.

EXAMPLE 5

Identification of a Test Compound which Decreases WEE1-like Serine/Threonine Protein Kinase Activity A test compound is administered to a culture of human cells transfected with a WEE1-like serine/threonine protein kinase expression construct and incubated at 37° C. for 10 to 45 minutes. A culture of the same type of cells that have not been transfected is incubated for the same time without the test compound to provide a negative control. WEE1-like serine/threonine protein kinase activity is measured using the method of Nakanishi et al., Genes Cells 2000 October; 5(10): 839–47; Fattaey & Booher, Prog Cell Cycle Res 1997; 3:233–40; or Den Haese et al., Mol Biol Cell 1995 April; 6(4):371–85.

A test compound which decreases the WEE1-like serine/threonine protein kinase activity of the WEE1-like serine/threonine protein kinase relative to the WEE1-like serine/threonine protein kinase activity in the absence of the test compound is identified as an inhibitor of WEE1-like serine/threonine protein kinase activity.

EXAMPLE 6

Tissue-specific Expression of WEE1-like Serine/Threonine Protein Kinase

The qualitative expression pattern of WEE1-like serine/threonine protein kinase in various tissues is determined by Reverse Transcription-Polymerase Chain Reaction (RT-PCR).

To demonstrate that WEE1-like serine/threonine protein kinase is involved in the disease process of COPD, the initial expression panel consists of RNA samples from respiratory tissues and inflammatory cells relevant to COPD: lung (adult and fetal), trachea, freshly isolated alveolar type II cells, cultured human bronchial epithelial cells, cultured small airway epithelial cells, cultured bronchial sooth muscle cells, cultured H441 cells (Clara-like), freshly isolated neutrophils and monocytes, and cultured monocytes (macrophage-like). Body map profiling also is carried out, using total RNA panels purchased from Clontech. The tissues are adrenal gland, bone marrow, brain, colon, heart, kidney, liver, lung, mammary gland, pancreas, prostate, salivary gland, skeletal muscle, small intestine, spleen, stomach, testis, thymus, trachea, thyroid, and uterus.

To demonstrate that WEE1-like serine/threonine protein kinase is involved in peripheral or central nervous system disorders, the following tissues are screened: fetal and adult brain, muscle, heart, lung, kidney, liver, thymus, testis, colon, placenta, trachea, pancreas, kidney, gastric mucosa, colon, liver, cerebellum, skin, cortex (Alzheimer's and normal), hypothalamus, cortex, amygdala, cerebellum, hippocampus, choroid, plexus, thalamus, and spinal cord.

To demonstrate that WEE1-like serine/threonine protein kinase is involved in cancer, expression is determined in the following tissues: adrenal gland, bone marrow, brain, cerebellum, colon, fetal brain, fetal liver, heart, kidney, liver, lung, mammary gland, pancreas, placenta, prostate, salivary gland, skeletal muscle, small intestine, spinal cord, spleen, stomach, testis, thymus, thyroid, trachea, uterus, and peripheral blood lymphocytes. Expression in the following cancer cell lines also is determined: DU-145 (prostate), NCI-H125 (lung), HT-29 (colon), COLO-205 (colon), A-549 (lung), NCI-H460 (lung), HT-116 (colon), DLD-1 (colon), MDA-MD-231 (breast), LS174T (colon), ZF-75 (breast), MDA-MN-435 (breast), HT-1080, MCF-7 (breast), and U87. Matched pairs of malignant and normal tissue from the same patient also are tested.

Quantitative Expression Profiling

Quantitative expression profiling is performed by the form of quantitative PCR analysis called "kinetic analysis" firstly described in Higuchi et al., *BioTechnology* 10, 413–17, 1992, and Higuchi et al., *BioTechnology* 11, 1026–30, 1993. The principle is that at any given cycle within the exponential phase of PCR, the amount of product is proportional to the initial number of template copies.

If the amplification is performed in the presence of an internally quenched fluorescent oligonucleotide (TaqMan probe) complementary to the target sequence, the probe is cleaved by the 5'-3' endonuclease activity of Taq DNA polymerase and a fluorescent dye released in the medium (Holland et al., *Proc. Natl. Acad. Sci. U.S.A.* 88, 7276–80, 1991). Because the fluorescence emission will increase in direct proportion to the amount of the specific amplified product, the exponential growth phase of PCR product can be detected and used to determine the initial template concentration (Heid et al., *Genome Res.* 6, 986–94, 1996, and Gibson et al., *Genome Res.* 6, 995–1001, 1996).

The amplification of an endogenous control can be performed to standardize the amount of sample RNA added to a reaction. In this kind of experiment, the control of choice is the 18S ribosomal RNA. Because reporter dyes with differing emission spectra are available, the target and the endogenous control can be independently quantified in the same tube if probes labeled with different dyes are used.

All "real time PCR" measurements of fluorescence are made in the ABI Prism 7700.

RNA Extraction and cDNA Preparation

Total RNA from the tissues listed above are used for expression quantification. RNAs labeled "from autopsy" were extracted from autoptic tissues with the TRIzol reagent (Life Technologies, MD) according to the manufacturer's protocol.

50 µg of each RNA were treated with DNase I for 1 hour at 37° C. in the following reaction mix: 0.2 U/µl RNase-free DNase I (Roche Diagnostics, Germany); 0.4 U/µl RNase inhibitor (PE Applied Biosystems, CA); 10 mM Tris-HCl pH 7.9; 10 mM $MgCl_2$; 50 mM NaCl; and 1 mM DTT.

After incubation, RNA is extracted once with 1 volume of phenol:chloroform:isoamyl alcohol (24:24:1) and once with chloroform, and precipitated with 1/10 volume of 3 M sodium acetate, pH5.2, and 2 volumes of ethanol.

50 µg of each RNA from the autoptic tissues are DNase treated with the DNA-free kit purchased from Ambion (Ambion, Tex.). After resuspension and spectrophotometric quantification, each sample is reverse transcribed with the TaqMan Reverse Transcription Reagents (PE Applied Biosystems, CA) according to the manufacturer's protocol. The final concentration of RNA in the reaction mix is 200 ng/µL. Reverse transcription is carried out with 2.5 µM of random hexamer primers.

TaqMan Quantitative Analysis

Specific primers and probe are designed according to the recommendations of PE Applied Biosystems; the probe can be labeled at the 5' end FAM (6-carboxy-fluorescein) and at the 3' end with TAMRA (6-carboxy-tetramethyl-rhodamine). Quantification experiments are performed on 10 ng of reverse transcribed RNA from each sample. Each determination is done in triplicate.

Total cDNA content is normalized with the simultaneous quantification (multiplex PCR) of the 18S ribosomal RNA using the Pre-Developed TaqMan Assay Reagents (PDAR) Control Kit (PE Applied Biosystems, CA).

The assay reaction mix is as follows: 1× final TaqMan Universal PCR Master Mix (from 2× stock) (PE Applied Biosystems, CA); 1×PDAR control—18S RNA (from 20× stock); 300 nM forward primer; 900 nM reverse primer; 200 nM probe; 10 ng cDNA; and water to 25 µl.

Each of the following steps are carried out once: pre PCR, 2 minutes at 50° C., and 10 minutes at 95° C. The following steps are carried out 40 times denaturation, 15 seconds at 95° C., annealing/extension, 1 minute at 60° C.

The experiment is performed on an ABI Prism 7700 Sequence Detector (PE Applied Biosystems, CA). At the end of the run, fluorescence data acquired during PCR are processed as described in the ABI Prism 7700 user's manual in order to achieve better background subtraction as well as signal linearity with the starting target quantity.

EXAMPLE 7

Proliferation Inhibition Assay: Antisense Oligonucleotides Suppress the Growth of Cancer Cell Lines The cell line used for testing is the human colon cancer cell line HCT116. Cells are cultured in RPMI-1640 with 10–15% fetal calf serum at a concentration of 10,000 cells per milliliter in a volume of 0.5 ml and kept at 37° C. in a 95% air/5% $CO_2$ atmosphere.

Phosphorothioate oligoribonucleotides are synthesized on an Applied Biosystems Model 380B DNA synthesizer using phosphoroamidite chemistry. A sequence of 24 bases complementary to the nucleotides at position 1 to 24 of SEQ ID NO:1 is used as the test oligonucleotide. As a control, another (random) sequence is used: 5'-TCA ACT GAC TAG ATG TAC ATG GAC-3'. Following assembly and deprotection, oligonucleotides are ethanol-precipitated twice, dried, and suspended in phosphate buffered saline at the desired concentration. Purity of the oligonucleotides is tested by capillary gel electrophoresis and ion exchange HPLC. The purified oligonucleotides are added to the culture medium at a concentration of 10 μM once per day for seven days.

The addition of the test oligonucleotide for seven days results in significantly reduced expression of human WEE1-like serine/threonine protein kinase as determined by Western blotting. This effect is not observed with the control oligonucleotide. After 3 to 7 days, the number of cells in the cultures is counted using an automatic cell counter. The number of cells in cultures treated with the test oligonucleotide (expressed as 100%) is compared with the number of cells in cultures treated with the control oligonucleotide. The number of cells in cultures treated with the test oligonucleotide is not more than 30% of control, indicating that the inhibition of human WEE1-like serine/threonine protein kinase has an anti-proliferative effect on cancer cells.

EXAMPLE 8

In vivo Testing of Compounds/Target Validation

1. Acute Mechanistic Assays 1.1. Reduction in Mitogenic Plasma Hormone Levels

This non-tumor assay measures the ability of a compound to reduce either the endogenous level of a circulating hormone or the level of hormone produced in response to a biologic stimulus. Rodents are administered test compound (p.o., i.p., i.v., i.m., or s.c.). At a predetermined time after administration of test compound, blood plasma is collected. Plasma is assayed for levels of the hormone of interest. If the normal circulating levels of the hormone are too low and/or variable to provide consistent results, the level of the hormone may be elevated by a pre-treatment with a biologic stimulus (i.e., LHRH may be injected i.m. into mice at a dosage of 30 ng/mouse to induce a burst of testosterone synthesis). The timing of plasma collection would be adjusted to coincide with the peak of the induced hormone response. Compound effects are compared to a vehicle-treated control group. An F-test is preformed to determine if the variance is equal or unequal followed by a Student's t-test. Significance is p value $\leq 0.05$ compared to the vehicle control group.

1.2. Hollow Fiber Mechanism of Action Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol, these may include assays for gene expression (bDNA, PCR, or Taqman), or a specific biochemical activity (i.e., cAMP levels. Results are analyzed by Student's t-test or Rank Sum test after the variance between groups is compared by an F-test, with significance at $p \leq 0.05$ as compared to the vehicle control group.

2. Subacute Functional In Vivo Assays 2.1. Reduction in Mass of Hormone Dependent Tissues This is another non-tumor assay that measures the ability of a compound to reduce the mass of a hormone dependent tissue (i.e., seminal vesicles in males and uteri in females). Rodents are administered test compound (p.o., i.p., i.v., i.m., or s.c.) according to a predetermined schedule and for a predetermined duration (i.e., 1 week). At termination of the study, animals are weighed, the target organ is excised, any fluid is expressed, and the weight of the organ is recorded. Blood plasma may also be collected. Plasma may be assayed for levels of a hormone of interest or for levels of test agent. Organ weights may be directly compared or they may be normalized for the body weight of the animal. Compound effects are compared to a vehicle-treated control group. An F-test is preformed to determine if the variance is equal or unequal followed by a Student's t-test. Significance is p value $\leq 0.05$ compared to the vehicle control group.

2.2. Hollow Fiber Proliferation Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol. Cell proliferation is determined by measuring a marker of cell number (i.e., MTT or LDH). The cell number and change in cell number from the starting inoculum are analyzed by Student's t-test or Rank Sum test after the variance between groups is compared by an F-test, with significance at $p \leq 0.05$ as compared to the vehicle control group.

2.3. Anti-angiogenesis Models 2.3.1. Corneal Angiogenesis

Hydron pellets with or without growth factors or cells are implanted into a micropocket surgically created in the rodent cornea. Compound administration may be systemic or local (compound mixed with growth factors in the hydron pellet). Corneas are harvested at 7 days post implantation immediately following intracardiac infusion of colloidal carbon and are fixed in 10% formalin. Readout is qualitative scoring and/or image analysis. Qualitative scores are compared by Rank Sum test. Image analysis data is evaluated by measuring the area of neovascularization (in pixels) and group averages are compared by Student's t-test (2 tail). Significance is $p \leq 0.05$ as compared to the growth factor or cells only group.

2.3.2. Matrigel Angiogenesis

Matrigel, containing cells or growth factors, is injected subcutaneously. Compounds are administered p.o., i.p., i.v., i.m., or s.c. Matrigel plugs are harvested at predetermined time point(s) and prepared for readout. Readout is an ELISA-based assay for hemoglobin concentration and/or histological examination (i.e. vessel count, special staining for endothelial surface markers: CD31, factor-8). Readouts are analyzed by Student's t-test, after the variance between groups is compared by an F-test, with significance determined at $p \leq 0.05$ as compared to the vehicle control group.

3. Primary Antitumor Efficacy

3.1. Early Therapy Models

3.1.1. Subcutaneous Tumor

Tumor cells or fragments are implanted subcutaneously on Day 0. Vehicle and/or compounds are administered p.o., i.p., i.v., i.m., or s.c. according to a predetermined schedule starting at a time, usually on Day 1, prior to the ability to measure the tumor burden. Body weights and tumor measurements are recorded 2–3 times weekly. Mean net body and tumor weights are calculated for each data collection day. Anti-tumor efficacy may be initially determined by comparing the size of treated (T) and control (C) tumors on a given day by a Student's t-test, after the variance between groups is compared by an F-test, with significance determined at $p \leq 0.05$. The experiment may also be continued past the end of dosing in which case tumor measurements would continue to be recorded to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is $p \leq 0.05$.

3.1.2. Intraperitoneal/Intracranial Tumor Models

Tumor cells are injected intraperitoneally or intracranially on Day 0. Compounds are administered p.o., i.p., i.v., i.m., or s.c. according to a predetermined schedule starting on Day 1. Observations of morbidity and/or mortality are recorded twice daily. Body weights are measured and recorded twice weekly. Morbidity/mortality data is expressed in terms of the median time of survival and the number of long-term survivors is indicated separately. Survival times are used to generate Kaplan-Meier curves. Significance is $p \leq 0.05$ by a log-rank test compared to the control group in the experiment.

3.2. Established Disease Model

Tumor cells or fragments are implanted subcutaneously and grown to the desired size for treatment to begin. Once at the predetermined size range, mice are randomized into treatment groups. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group. Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group.

3.3. Orthotopic Disease Models

3.3.1. Mammary Fat Pad Assay

Tumor cells or fragments, of mammary adenocarcinoma origin, are implanted directly into a surgically exposed and reflected mammary fat pad in rodents. The fat pad is placed back in its original position and the surgical site is closed. Hormones may also be administered to the rodents to support the growth of the tumors. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group.

Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group. In addition, this model provides an opportunity to increase the rate of spontaneous metastasis of this type of tumor. Metastasis can be assessed at termination of the study by counting the number of visible foci per target organ, or measuring the target organ weight. The means of these endpoints are compared by Student's t-test after conducting an F-test, with significance determined at $p \leq 0.05$ compared to the control group in the experiment.

3.3.2. Intraprostatic Assay

Tumor cells or fragments, of prostatic adenocarcinoma origin, are implanted directly into a surgically exposed dorsal lobe of the prostate in rodents. The prostate is externalized through an abdominal incision so that the tumor can be implanted specifically in the dorsal lobe while verifying that the implant does not enter the seminal vesicles. The successfully inoculated prostate is replaced in the abdomen and the incisions through the abdomen and skin are closed. Hormones may also be administered to the rodents to support the growth of the tumors. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the lungs), or measuring the target organ weight (i.e., the regional lymph nodes). The means of these endpoints are compared by Student's t-test after conducting an F-test, with significance determined at $p \leq 0.05$ compared to the control group in the experiment.

3.3.3. Intrabronchial Assay

Tumor cells of pulmonary origin may be implanted intrabronchially by making an incision through the skin and exposing the trachea. The trachea is pierced with the beveled end of a 25 gauge needle and the tumor cells are inoculated into the main bronchus using a flat-ended 27 gauge needle with a 90° bend. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the contralateral lung), or measuring the target organ weight. The means of these endpoints are compared by Student's t-test after conducting an F-test, with significance determined at $p \leq 0.05$ compared to the control group in the experiment.

3.3.4. Intracecal Assay

Tumor cells of gastrointestinal origin may be implanted intracecally by making an abdominal incision through the skin and externalizing the intestine. Tumor cells are inoculated into the cecal wall without penetrating the lumen of the intestine using a 27 or 30 gauge needle. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the liver), or measuring the target organ weight. The means of these endpoints are compared by Student's t-test after conducting an F-test, with significance determined at $p \leq 0.05$ compared to the control group in the experiment.

4. Secondary (Metastatic) Antitumor Efficacy 4.1. Spontaneous Metastasis

Tumor cells are inoculated s.c. and the tumors allowed to grow to a predetermined range for spontaneous metastasis studies to the lung or liver. These primary tumors are then excised. Compounds are administered p.o., i.p., i.v., i.m., or s.c. according to a predetermined schedule which may include the period leading up to the excision of the primary tumor to evaluate therapies directed at inhibiting the early stages of tumor metastasis. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance determined at $p \leq 0.05$ compared to the control group in the experiment for both of these endpoints.

4.2. Forced Metastasis

Tumor cells are injected into the tail vein, portal vein, or the left ventricle of the heart in experimental (forced) lung, liver, and bone metastasis studies, respectively. Compounds are administered p.o., i.p., i.v., i.m., or s.c. according to a predetermined schedule. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance at $p \leq 0.05$ compared to the vehicle control group in the experiment for both endpoints.

EXAMPLE 9

In vivo Testing of Compounds/Target Validation

1. Pain:

Acute Pain

Acute pain is measured on a hot plate mainly in rats. Two variants of hot plate testing are used: In the classical variant animals are put on a hot surface (52 to 56° C.) and the latency time is measured until the animals show nocifensive behavior, such as stepping or foot licking. The other variant is an increasing temperature hot plate where the experimental animals are put on a surface of neutral temperature. Subsequently this surface is slowly but constantly heated until the animals begin to lick a hind paw. The temperature which is reached when hind paw licking begins is a measure for pain threshold.

Compounds are tested against a vehicle treated control group. Substance application is performed at different time points via different application routes (i.v., i.p., p.o., i.t., i.c.v., s.c., intradermal, transdermal) prior to pain testing.

Persistent Pain

Persistent pain is measured with the formalin or capsaicin test, mainly in rats. A solution of 1 to 5% formalin or 10 to 100 µg capsaicin is injected into one hind paw of the experimental animal. After formalin or capsaicin application the animals show nocifensive reactions like flinching, licking and biting of the affected paw. The number of nocifensive reactions within a time frame of up to 90 minutes is a measure for intensity of pain.

Compounds are tested against a vehicle treated control group. Substance application is performed at different time points via different application routes (i.v., i.p., p.o., i.t., i.c.v., s.c., intradermal, transdermal) prior to formalin or capsaicin administration.

Neuropathic Pain

Neuropathic pain is induced by different variants of unilateral sciatic nerve injury mainly in rats. The operation is performed under anesthesia. The first variant of sciatic nerve injury is produced by placing loosely constrictive ligatures around the common sciatic nerve. The second variant is the tight ligation of about the half of the diameter of the common sciatic nerve. In the next variant, a group of models is used in which tight ligations or transections are made of either the L5 and L6 spinal nerves, or the L % spinal nerve only. The fourth variant involves an axotomy of two of the three terminal branches of the sciatic nerve (tibial and common peroneal nerves) leaving the remaining sural nerve intact whereas the last variant comprises the axotomy of only the tibial branch leaving the sural and common nerves uninjured. Control animals are treated with a sham operation.

Postoperatively, the nerve injured animals develop a chronic mechanical allodynia, cold allodynioa, as well as a thermal hyperalgesia. Mechanical allodynia is measured by means of a pressure transducer (electronic von Frey Anesthesiometer, IITC Inc.-Life Science Instruments, Woodland Hills, SA, USA; Electronic von Frey System, Somedic Sales AB, Hörby, Sweden). Thermal hyperalgesia is measured by means of a radiant heat source (Plantar Test, Ugo Basile, Comerio, Italy), or by means of a cold plate of 5 to 10° C. where the nocifensive reactions of the affected hind paw are counted as a measure of pain intensity. A further test for cold induced pain is the counting of nocifensive reactions, or duration of nocifensive responses after plantar administration of acetone to the affected hind limb. Chronic pain in general is assessed by registering the circadian rhythms in activity (Surjo and Arndt, Universität zu Köln, Cologne, Germany), and by scoring differences in gait (foot print patterns; FOOTPRINTS program, Klapdor et al., 1997. A low cost method to analyze footprint patterns. J. Neurosci. Methods 75, 49–54).

Compounds are tested against sham operated and vehicle treated control groups. Substance application is performed at different time points via different application routes (i.v., i.p., p.o., i.t., i.c.v., s.c., intradermal, transdermal) prior to pain testing.

Inflammatory Pain

Inflammatory pain is induced mainly in rats by injection of 0.75 mg carrageenan or complete Freund's adjuvant into one hind paw. The animals develop an edema with mechanical allodynia as well as thermal hyperalgesia. Mechanical allodynia is measured by means of a pressure transducer (electronic von Frey Anesthesiometer, IITC Inc.-Life Science Instruments, Woodland Hills, SA, USA). Thermal hyperalgesia is measured by means of a radiant heat source (Plantar Test, Ugo Basile, Comerio, Italy, Paw thermal stimulator, G. Ozaki, University of California, USA). For edema measurement two methods are being used. In the first method, the animals are sacrificed and the affected hindpaws sectioned and weighed. The second method comprises differences in paw volume by measuring water displacement in a plethysmometer (Ugo Basile, Comerio, Italy).

Compounds are tested against uninflamed as well as vehicle treated control groups. Substance application is performed at different time points via different application routes (i.v., i.p., p.o., i.t., i.c.v., s.c., intradermal, transdermal) prior to pain testing.

Diabetic Neuropathic Pain

Rats treated with a single intraperitoneal injection of 50 to 80 mg/kg streptozotocin develop a profound hyperglycemia and mechanical allodynia within 1 to 3 weeks. Mechanical allodynia is measured by means of a pressure transducer (electronic von Frey Anesthesiometer, IITC Inc.-Life Science Instruments, Woodland Hills, SA, USA).

Compounds are tested against diabetic and non-diabetic vehicle treated control groups. Substance application is performed at different time points via different application routes (i.v., i.p., p.o., i.t., i.c.v., s.c., intradermal, transdermal) prior to pain testing.

2. Parkinson's Disease

6-Hydroxydopamine (6-OH-DA) Lesion

Degeneration of the dopaminergic nigrostriatal and striatopallidal pathways is the central pathological event in Parkinson's disease. This disorder has been mimicked experimentally in rats using single/sequential unilateral stereotaxic injections of 6-OH-DA into the medium forebrain bundle (MFB).

Male Wistar rats (Harlan Winkelmann, Germany), weighing 200±250 g at the beginning of the experiment, are used. The rats are maintained in a temperature- and humidity-controlled environment under a 12 h light/dark cycle with free access to food and water when not in experimental sessions. The following in vivo protocols are approved by the governmental authorities. All efforts are made to minimize animal suffering, to reduce the number of animals used, and to utilize alternatives to in vivo techniques.

Animals are administered pargyline on the day of surgery (Sigma, St. Louis, Mo., USA; 50 mg/kg i.p.) in order to inhibit metabolism of 6-OHDA by monoamine oxidase and desmethylimipramine HCl (Sigma; 25 mg/kg i.p.) in order to prevent uptake of 6-OHDA by noradrenergic terminals. Thirty minutes later the rats are anesthetized with sodium pentobarbital (50 mg/kg) and placed in a stereotaxic frame. In order to lesion the DA nigrostriatal pathway 4 μl of 0.01% ascorbic acid-saline containing 8 μg of 6-OHDA HBr (Sigma) are injected into the left medial fore-brain bundle at a rate of 1 μl/min (2.4 mm anterior, 1.49 mm lateral, −2.7 mm ventral to Bregma and the skull surface). The needle is left in place an additional 5 min to allow diffusion to occur.

Stepping Test

Forelimb akinesia is assessed three weeks following lesion placement using a modified stepping test protocol. In brief, the animals are held by the experimenter with one hand fixing the hindlimbs and slightly raising the hind part above the surface. One paw is touching the table, and is then moved slowly sideways (5 s for 1 m), first in the forehand and then in the backhand direction. The number of adjusting steps is counted for both paws in the backhand and forehand direction of movement. The sequence of testing is right paw forehand and backhand adjusting stepping, followed by left paw forehand and backhand directions. The test is repeated three times on three consecutive days, after an initial training period of three days prior to the first testing. Forehand adjusted stepping reveals no consistent differences between lesioned and healthy control animals. Analysis is therefore restricted to backhand adjusted stepping.

Balance Test

Balance adjustments following postural challenge are also measured during the stepping test sessions. The rats are held in the same position as described in the stepping test and, instead of being moved sideways, tilted by the experimenter towards the side of the paw touching the table. This maneuver results in loss of balance and the ability of the rats to regain balance by forelimb movements is scored on a scale ranging from 0 to 3. Score 0 is given for a normal forelimb placement. When the forelimb movement is delayed but recovery of postural balance detected, score 1 is given. Score 2 represents a clear, yet insufficient, forelimb reaction, as evidenced by muscle contraction, but lack of success in recovering balance, and score 3 is given for no reaction of movement. The test is repeated three times a day on each side for three consecutive days after an initial training period of three days prior to the first testing.

Staircase Test (Paw Reaching)

A modified version of the staircase test is used for evaluation of paw reaching behavior three weeks following primary and secondary lesion placement. Plexiglass test boxes with a central platform and a removable staircase on each side are used. The apparatus is designed such that only the paw on the same side at each staircase can be used, thus providing a measure of independent forelimb use. For each test the animals are left in the test boxes for 15 min. The double staircase is filled with 7×3 chow pellets (Precision food pellets, formula: P, purified rodent diet, size 45 mg; Sandown Scientific) on each side. After each test the number of pellets eaten (successfully retrieved pellets) and the number of pellets taken (touched but dropped) for each paw and the success rate (pellets eaten/pellets taken) are counted separately. After three days of food deprivation (12 g per animal per day) the animals are tested for 11 days. Full analysis is conducted only for the last five days.

MPTP treatment

The neurotoxin 1-methyl-4-phenyl-1,2,3,6-tetrahydro-pyridine (MPTP) causes degeneration of mesencephalic dopaminergic (DAergic) neurons in rodents, non-human primates, and humans and, in so doing, reproduces many of the symptoms of Parkinson's disease. MPTP leads to a marked decrease in the levels of dopamine and its metabolites, and in the number of dopaminergic terminals in the striatum as well as severe loss of the tyrosine hydroxylase (TH)-immunoreactive cell bodies in the substantia nigra, pars compacta.

In order to obtain severe and long-lasting lesions, and to reduce mortality, animals receive single injections of MPTP, and are then tested for severity of lesion 7–10 days later. Successive MPTP injections are administered on days 1, 2 and 3. Animals receive application of 4 mg/kg MPTP hydrochloride (Sigma) in saline once daily. All injections are intraperitoneal (i.p.) and the MPTP stock solution is frozen between injections. Animals are decapitated on day 11.

Immunohistology

At the completion of behavioral experiments, all animals are anaesthetized with 3 ml thiopental (1 g/40 ml i.p., Tyrol Pharma). The mice are perfused transcardially with 0.01 M PBS (pH 7.4) for 2 min, followed by 4% paraformaldehyde (Merck) in PBS for 15 min. The brains are removed and placed in 4% paraformaldehyde for 24 h at 4° C. For dehydration they are then transferred to a 20% sucrose (Merck) solution in 0.1 M PBS at 4° C. until they sink. The brains are frozen in methylbutan at −20° C. for 2 min and stored at −70° C. Using a sledge microtome (mod. 3800-Frigocut, Leica), 25 μm sections are taken from the genu of the corpus callosum (AP 1.7 mm) to the hippocampus (AP 21.8 mm) and from AP 24.16 to AP 26.72. Forty-six sections are cut and stored in assorters in 0.25 M Tris buffer (pH 7.4) for immunohistochemistry.

A series of sections is processed for free-floating tyrosine hydroxylase (TH) immunohistochemistry. Following three rinses in 0.1 M PBS, endogenous peroxidase activity is quenched for 10 min in 0.3% $H_2O_2$±PBS. After rinsing in PBS, sections are preincubated in 10% normal bovine serum (Sigma) for 5 min as blocking agent and transferred to either primary anti-rat TH rabbit antiserum (dilution 1:2000).

Following overnight incubation at room temperature, sections for TH immunoreactivity are rinsed in PBS (2×10 min) and incubated in biotinylated anti-rabbit immunoglobulin G raised in goat (dilution 1:200) (Vector) for 90 min, rinsed repeatedly and transferred to Vectastain ABC (Vector) solution for 1 h. 3,3'-Diaminobenzidine tetrahydrochloride (DAB; Sigma) in 0.1 M PBS, supplemented with 0.005% $H_2O_2$, serves as chromogen in the subsequent visualization reaction. Sections are mounted on to gelatin-coated slides, left to dry overnight, counter-stained with hematoxylin dehydrated in ascending alcohol concentrations and cleared in butylacetate. Coverslips are mounted on entellan.

Rotarod Test

We use a modification of the procedure described by Rozas and Labandeira-Garcia (1997), with a CR-1 Rotamex system (Columbus Instruments, Columbus, Ohio) comprising an IBM-compatible personal computer, a CIO-24 data acquisition card, a control unit, and a four-lane rotarod unit. The rotarod unit consists of a rotating spindle (diameter 7.3 cm) and individual compartments for each mouse. The system software allows preprogramming of session protocols with varying rotational speeds (0–80 rpm). Infrared beams are used to detect when a mouse has fallen onto the base grid beneath the rotarod. The system logs the fall as the end of the experiment for that mouse, and the total time on the rotarod, as well as the time of the fall and all the set-up parameters, are recorded. The system also allows a weak current to be passed through the base grid, to aid training.

3. Dementia

The Object Recognition Task

The object recognition task has been designed to assess the effects of experimental manipulations on the cognitive performance of rodents. A rat is placed in an open field, in which two identical objects are present. The rats inspects both objects during the first trial of the object recognition task. In a second trial, after a retention interval of for example 24 hours, one of the two objects used in the first trial, the 'familiar' object, and a novel object are placed in the open field. The inspection time at each of the objects is registered. The basic measures in the OR task is the time spent by a rat exploring the two object the second trial. Good retention is reflected by higher exploration times towards the novel than the 'familiar' object.

Administration of the putative cognition enhancer prior to the first trial predominantly allows assessment of the effects on acquisition, and eventually on consolidation processes. Administration of the testing compound after the first trial allows to assess the effects on consolidation processes, whereas administration before the second trial allows to measure effects on retrieval processes.

The Passive Avoidance Task

The passive avoidance task assesses memory performance in rats and mice. The inhibitory avoidance apparatus consists of a two-compartment box with a light compartment and a dark compartment. The two compartments are separated by a guillotine door that can be operated by the experimenter. A threshold of 2 cm separates the two compartments when the guillotine door is raised. When the door is open, the illumination in the dark compartment is about 2 lux. The light intensity is about 500 lux at the center of the floor of the light compartment.

Two habituation sessions, one shock session, and a retention session are given, separated by inter-session intervals of 24 hours. In the habituation sessions and the retention session the rat is allowed to explore the apparatus for 300 sec. The rat is placed in the light compartment, facing the wall opposite to the guillotine door. After an accommodation period of 15 sec. the guillotine door is opened so that all parts of the apparatus can be visited freely. Rats normally avoid brightly lit areas and will enter the dark compartment within a few seconds.

In the shock session the guillotine door between the compartments is lowered as soon as the rat has entered the dark compartment with its four paws, and a scrambled 1 mA footshock is administered for 2 sec. The rat is removed from the apparatus and put back into its home cage. The procedure during the retention session is identical to that of the habituation sessions.

The step-through latency, that is the first latency of entering the dark compartment (in sec.) during the retention session is an index of the memory performance of the animal; the longer the latency to enter the dark compartment, the better the retention is. A testing compound in given half an hour before the shock session, together with 1 mg*kg$^{-1}$ scopolamine. Scopolamine impairs the memory performance during the retention session 24 hours later. If the test compound increases the enter latency compared with the scopolamine-treated controls, is likely to possess cognition enhancing potential.

The Morris Water Escape Task

The Morris water escape task measures spatial orientation learning in rodents. It is a test system that has extensively been used to investigate the effects of putative therapeutic on the cognitive functions of rats and mice. The performance of an animal is assessed in a circular water tank with an escape platform that is submerged about 1 cm below the surface of the water. The escape platform is not visible for an animal swimming in the water tank. Abundant extra-maze cues are provided by the furniture in the room, including desks, computer equipment, a second water tank, the presence of the experimenter, and by a radio on a shelf that is playing softly.

The animals receive four trials during five daily acquisition sessions. A trial is started by placing an animal into the pool, facing the wall of the tank. Each of four starting positions in the quadrants north, east, south, and west is used once in a series of four trials; their order is randomized. The escape platform is always in the same position. A trial is terminated as soon as the animal had climbs onto the escape platform or when 90 seconds have elapsed, whichever event occurs first. The animal is allowed to stay on the platform for 30 seconds. Then it is taken from the platform and the next trial is started. If an animal did not find the platform within 90 seconds it is put on the platform by the experimenter and is allowed to stay there for 30 seconds. After the fourth trial of the fifth daily session, an additional trial is given as a probe trial: the platform is removed, and the time the animal spends in the four quadrants is measured for 30 or 60 seconds. In the probe trial, all animals start from the same start position, opposite to the quadrant where the escape platform had been positioned during acquisition.

Four different measures are taken to evaluate the performance of an animal during acquisition training: escape latency, traveled distance, distance to platform, and swimming speed. The following measures are evaluated for the probe trial: time (s) in quadrants and traveled distance (cm) in the four quadrants. The probe trial provides additional information about how well an animal learned the position of the escape platform. If an animal spends more time and swims a longer distance in the quadrant where the platform had been positioned during the acquisition sessions than in any other quadrant, one concludes that the platform position has been learned well.

In order to assess the effects of putative cognition enhancing compounds, rats or mice with specific brain lesions which impair cognitive functions, or animals treated with compounds such as scopolamine or MK-801, which interfere with normal learning, or aged animals which suffer from cognitive deficits, are used.

The T-maze Spontaneous Alternation Task

The T-maze spontaneous alternation task (TeMCAT) assesses the spatial memory performance in mice. The start arm and the two goal arms of the T-maze are provided with guillotine doors which can be operated manually by the experimenter. A mouse is put into the start arm at the beginning of training. The guillotine door is closed. In the first trial, the 'forced trial', either the left or right goal arm is blocked by lowering the guillotine door. After the mouse has been released from the start arm, it will negotiate the maze, eventually enter the open goal arm, and return to the start position, where it will be confined for 5 seconds, by lowering the guillotine door. Then, the animal can choose freely between the left and right goal arm (all guillotine-doors opened) during 14 'free choice' trials. As soon a the mouse has entered one goal arm, the other one is closed. The mouse eventually returns to the start arm and is free to visit whichever go alarm it wants after having been confined to the start arm for 5 seconds. After completion of 14 free choice trials in one session, the animal is removed from the maze. During training, the animal is never handled.

The percent alternations out of 14 trials is calculated. This percentage and the total time needed to complete the first forced trial and the subsequent 14 free choice trials (in s) is analyzed. Cognitive deficits are usually induced by an injection of scopolamine, 30 min before the start of the training session. Scopolamine reduced the per-cent alternations to chance level, or below. A cognition enhancer, which is always administered before the training session, will at least partially, antagonize the scopolamine-induced reduction in the spontaneous alternation rate.

EXAMPLE 10

Expression Profiling in Human Tissues

Total cellular RNA was isolated from cells by one of two standard methods: (1) guanidine isothiocyanate/Cesium chloride density gradient centrifugation or (2) the Tri-Reagent protocol according to the manufacturer's specifications (Molecular Research Center, Inc., Cincinatti, Ohio). Total RNA prepared by the Tri-reagent protocol was treated with DNAse I to remove genomic DNA contamination.

For relative quantitation of the mRNA distribution of WEE1-like serine/threonine protein kinase, total RNA from each cell or tissue source was first reverse transcribed. Eighty-five µg of total RNA was reverse transcribed using 1 µmole random hexamer primers, 0.5 mM each of dATP, dCTP, dGTP, and dTTP (Qiagen, Hilden, Germany), 3000 U RnaseQut (Invitrogen, Groningen, Netherlands) in a final volume of 680 µl. The first strand synthesis buffer and Omniscript (2 u/µl) reverse transcriptase were from (Qiagen, Hilden, Germany). The reaction was incubated at 37° C. for 90 minutes and cooled on ice. The volume was adjusted to 6800 µl with water, yielding a final concentration of 12.5 ng/µl of starting RNA.

For relative quantitation of the distribution of WEE1-like serine/threonine protein kinase mRNA in cells and tissues the Perkin Elmer ABI Prism®. 7700 Sequence Detection system or Biorad iCycler was used according to the manufacturer's specifications and protocols. PCR reactions were set up to quantitate WEE1-like serine/threonine protein kinase and the housekeeping genes HPRT, GAPDH, beta-actin, and others. Forward and reverse primers and probe for the WEE1-like serine/threonine protein kinase were designed using the Perkin Elmer ABI Primer Express™, software and were synthesized by TibMolBiol (Berlin, Germany). The WEE1-like serine/threonine protein kinase forward primer sequence was: CAGGATTCAGAGGCAAAGGG. The WEE1-like serine/threonine protein kinase reverse primer sequence was ACCACCTTGGACTCCCCTTAGCAACG. The fluorogenic probe, labeled with FAM as the reporter dye and TAMRA as the quencher, is CGAAGATGTGTCGAGCTCATG.

The following reactions in a final volume of 25 µl were set up: 1× TaqMan buffer A, 5.5 mM MgCl2, 200 nM each of dATP, dCTP, dGTP, and dUTP, 0.025 U/µl AmpliTaq Gold™, 0.01 U/µl AmpErase UNG® and probe 1×, WEE1-like serine/threonine protein kinase forward and reverse primers each at 200 nM, 200 nM WEE1-like serine/threonine protein kinase FAM/TAMRA-labeled probe, and 5 µl of template cDNA. Thermal cycling parameters were 2 min HOLD at 50° C., 10 min HOLD at 95° C., followed by melting at 95° C. for 15 sec and annealing/extending at 60° C. for 1 min for each of 40 cycles.

Calculation of Corrected CT Values

The CT-value is calculated as described above. The CF-value is calculated as followed:

---

1. PCR reactions were set up to quantitate the housekeeping genes (HKG) for each cDNA sample.
2. $CT_{HKG}$-values were calculated as described above
3. CT-mean values of all HKG for each cDNA are calculated (n = number of HKG):
   ($CT_{HKG1}$-value + $CT_{HKG2}$-value + $CT_{HKG-X}$-value)/n = $CT_{cDNA-X}$-mean values (n = number of HKG)
4. ($CT_{cDNA-1}$-mean value + $CT_{cDNA-X}$-mean value)/y = $CT_{pannel}$-mean value (y = number of cDNAs)
5. $CT_{pannel}$-mean value − $CT_{cDNA-X}$-mean value = $CF_{cDNA-X}$
6. $CT_{cDNA-X}$ + $CF_{cDNA-X}$ = $CT_{cor-cDNA-X}$

---

Calculation of Relative Expression

Definition: highest $CT_{cor-DNA-X}\neq 40$ is defined as $CT_{cor-cDNA-X}$[high]

Relative Expression=$2e(CT_{cor-cDNA-X}[high]−CT_{cor-cDNA}$

Figure 10:
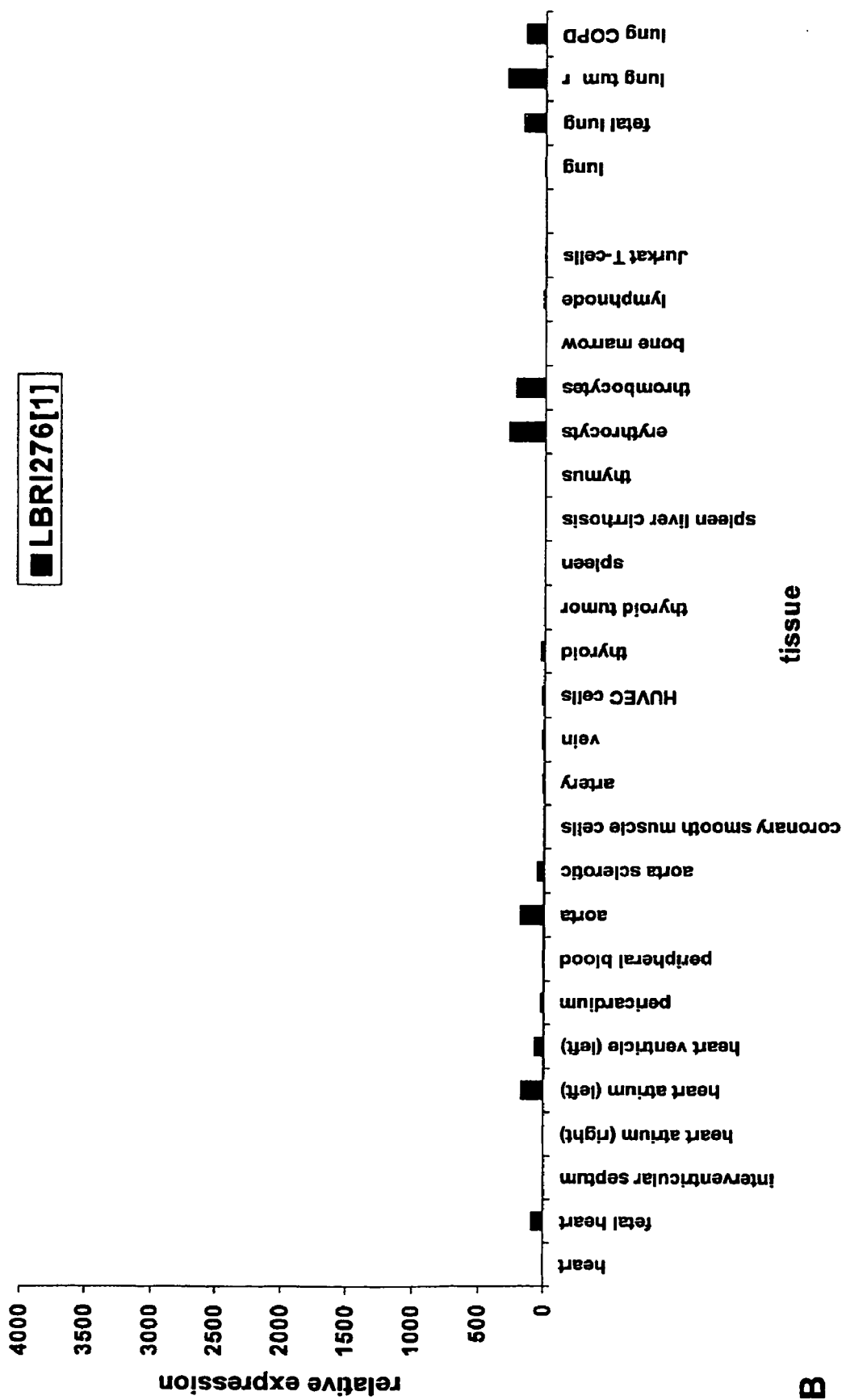
FIG. 10 shows the results of the WEE1-like protein kinase mRNA epression profiling in human tissues.
Figure 11:
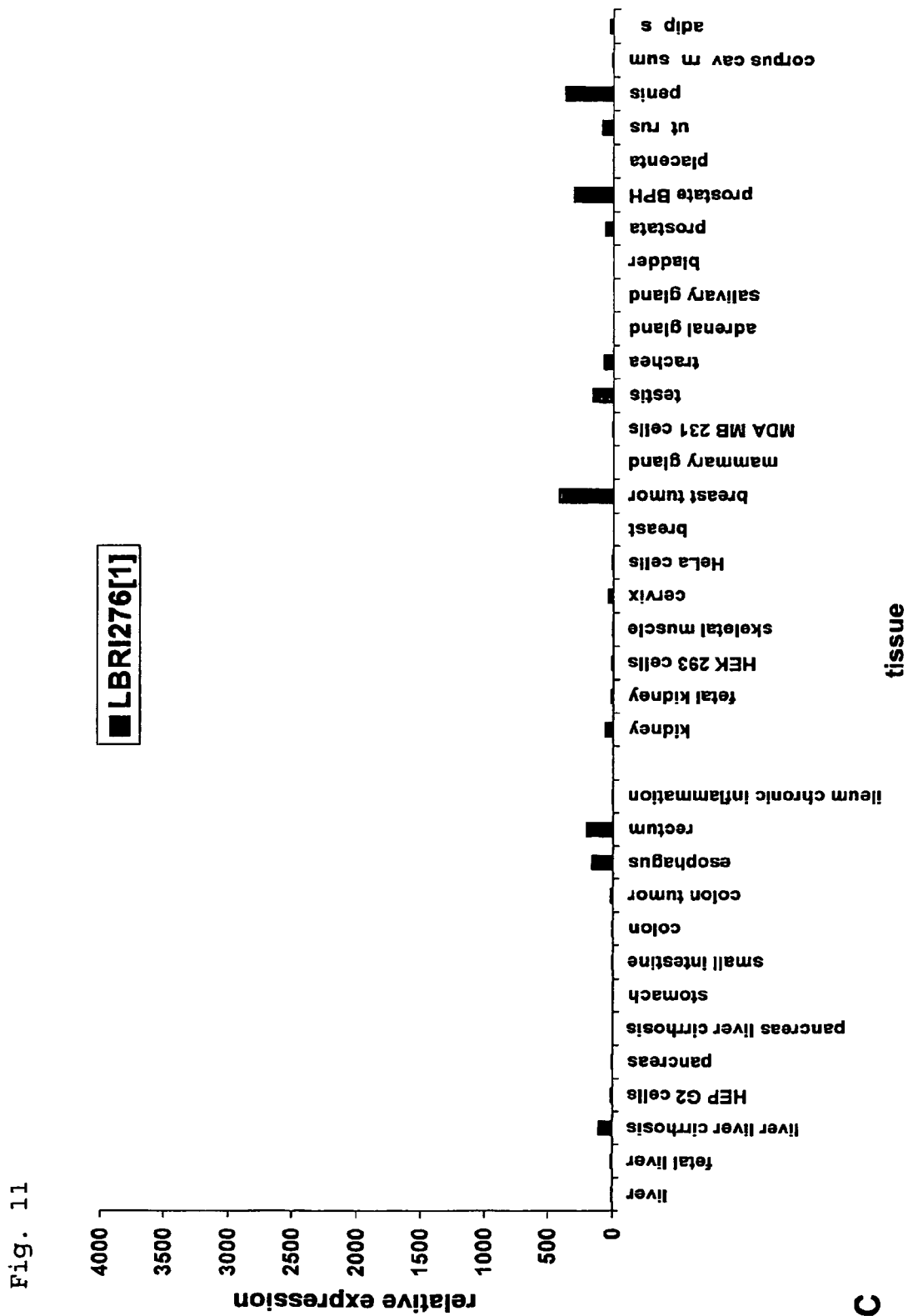
FIG. 11 shows the results of the WEE1-like protein kinase mRNA epression profiling in human tissues.

The results of the mRNA-quantification (expression profiling) are shown in FIGS. 9–11. Human WEE1-like serine/threonine protein kinase is expressed in different human tissues. The WEE1-like serine/threonine protein kinase is highly expressed in cerebellum, postcentral gyrus, cerebral meninges, thalamus, retina, dorsal root, ganglia, aorta, heart, erythrocyte, thrombocytes, lymph node, lung tumor, lung COPD, cervix, prostate BPH, breast tumor, penis.

The WEE1-like serine/threonine protein kinase is highly expressed in different brain tissues as cerebellum, postcentral gyrus, cerebral meninges, thalamus, retina, dorsal root ganglia. The expression in the above mentioned tissues suggests an association between WEE1-like serine/threonine protein kinase and peripheral and central nervous system diseases.

The WEE1-like serine/threonine protein kinase is highly expressed in lung tumor and breast tumor. The expression in the above mentioned tissues suggests an association between WEE1-like serine/threonine protein kinase and cancer.

The WEE1-like serine/threonine protein kinase is highly expressed in prostate BPH and penis. The expression in the above mentioned tissues suggests an association between WEE1-like serine/threonine protein kinase and genitourinary diseases.

The WEE1-like serine/threonine protein kinase is highly expressed in heart, aorta. The expression in the above mentioned tissues suggests an association between WEE1-like serine/threonine protein kinase and cardiovascular diseases.

The WEE1-like serine/threonine protein kinase is highly expressed in lung and lung COPD. The expression in the above mentioned tissues suggests an association between WEE1-like serine/threonine protein kinase and respiratory diseases.

EXAMPLE 11

Expression Profiling in Human Tissues Relevant for Diabetes and Obesity Pathophysiology RNA Extraction and cDNA Preparation Total RNA used for Taqman quantitative analysis were either purchased (Clontech, CA) or extracted from tissues using TRIzol reagent (Life Technologies, MD) according to a modified vendor protocol which utilizes the Rneasy protocol (Qiagen, CA)

One hundred µg of each RNA were treated with DNase I using RNase free—DNase (Qiagen, CA) for use with RNeasy or QiaAmp columns.

After elution and quantitation with Ribogreen (Molecular Probes Inc., OR) each sample was reverse transcribed using the GibcoBRL Superscript II First Strand Synthesis System for RT-PCR according to vendor protocol (Life Technologies, MD). The final concentration of RNA in the reaction mix was 50 ng/µL. Reverse transcription was performed with 50 ng of Random Hexamers.

TaqMan Quantitative Analysis

Specific primers and probe were designed according to PE Applied Biosystems' Primer Express program recommendations and are listed below:

```
forward primer:   5'-(TCCAGTGTCACACCCTCTCAAA)-3'
reverse primer:   5'-(TGTCACTGGGCAGCAGCTT)-3'
probe:            SYBR Green
```

The expected length of the PCR product was ~76 bp.

Quantitation experiments were performed on 25 ng of reverse transcribed RNA from each sample. 18S ribosomal RNA was measured as a control using the Pre-Developed TaqMan Assay Reagents (PDAR)(PE Applied Biosystems, CA). Assay reaction mix was as follows:

| | final |
|---|---|
| TaqMan SYBR Green PCR Master Mix (2×) (PE Applied Biosystems, CA) | 1× |
| Forward primer | 300 nM |
| Reverse primer | 300 nM |
| cDNA | 25 ng |
| Water to 25 uL | |
| PCR conditions: | |
| Once: | 2' minutes at 50° C. |
| | 10 minutes at 95° C. |
| 40 cycles: | 15 sec. at 95° C. |
| | 1 minute at 60° C. |

Figure 12:
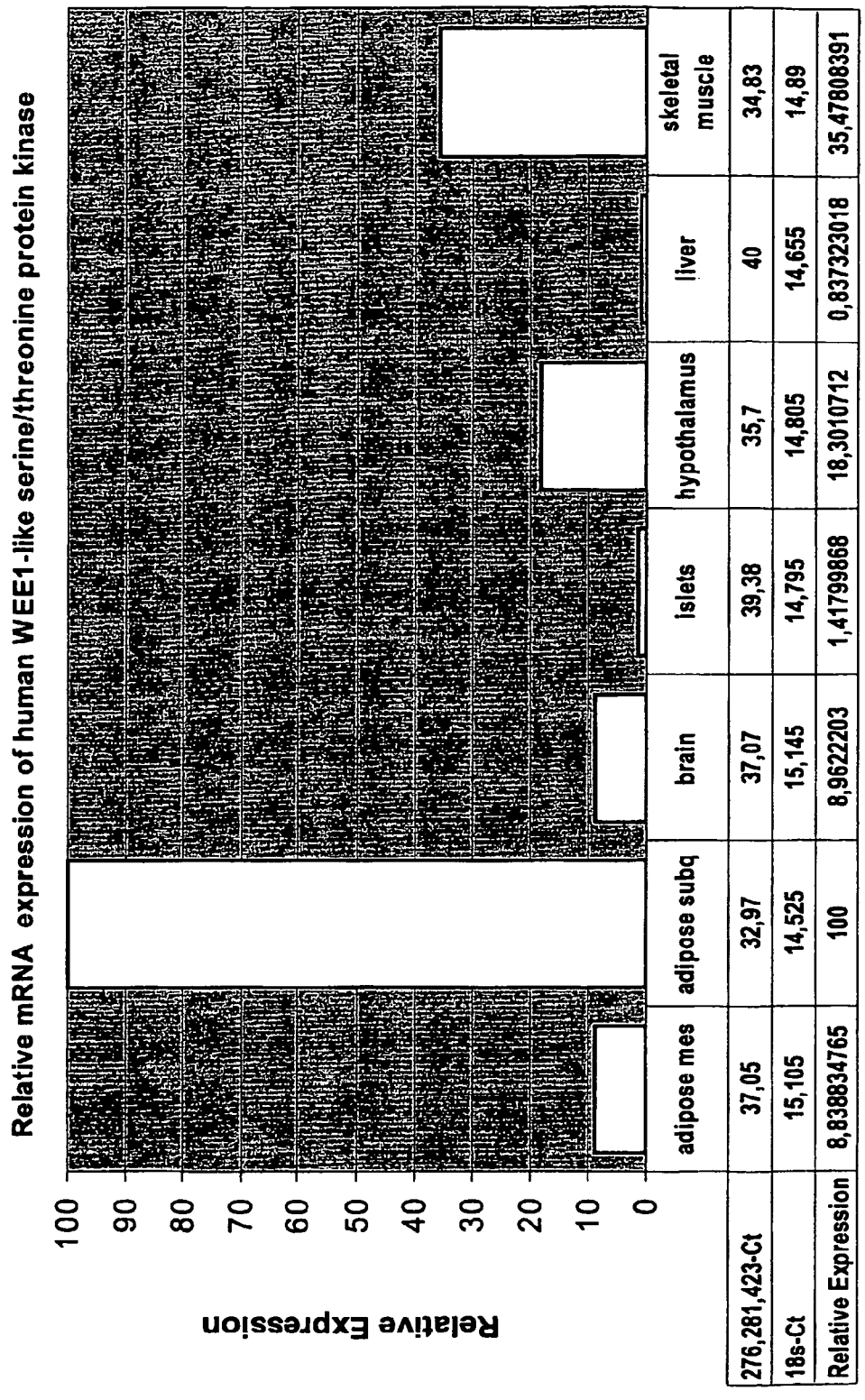
FIG. 12 shows the results of the WEE1-like protein kinase mRNA epression profiling in human tissues relevant for diabetes and obesity pathophysiology.

The experiment was performed on an ABI Prism 7700 Sequence Detector (PE Applied Biosystems, CA). At the end of the run, fluorescence data acquired during PCR were processed as described in the ABI Prism 7700 user's manual. Fold change was calculated using the delta-delta CT method with normalization to the 18S values. Relative expression was calculated by normalizing to 18 s (D Ct), then making the highest expressing tissue 100 and everything else relative to it. Copy number conversion was performed without normalization using the formula $Cn=10^{(Ct-40.007)/3.623}$. The results of the mRNA-quantification (expression profiling) are shown in FIG. 12.

REFERENCES

1. Mueller et al. (1995) Cell cycle regulation of a *Xenopus* Wee1-like kinase. Mol Biol Cell 6(1):119–34.
2. Watanabe et al. (1995) Regulation of the human WEE1Hu CDK tyrosine 15-kinase during the cell cycle. EMBO J 1;14(9):1878–91.
3. McGowan and Russell (1995) Cell cycle regulation of human WEE1. EMBO J 14(10):2166–75.
4. Hanks and Hunter (1995) Protein kinases 6. The eukaryotic protein kinase superfamily: kinase (catalytic) domain structure and classification. FASEB J 9(8):576–96.

---

The invention claimed is:

1. An isolated and purified protein comprising a first polypeptide segment comprising an amino acid sequence shown in SEQ ID NO:2.

2. The protein of claim 1 further comprising a second polypeptide segment comprising an amino acid sequence which is not an amino acid sequence shown in SEQ ID NO:2, wherein the second polypeptide segment is joined to the first polypeptide segment by means of a peptide bond.

3. An isolated and purified protein comprising an amino acid sequence which is at least 96% identical to an amino acid sequence shown as SEQ ID NO:2 and which has a kinase activity.

4. An isolated and purified polynucleotide which encodes the amino acid sequence shown in SEQ ID NO:2.

5. The polynucleotide of claim 4 which comprises the nucleotide sequence shown in SEQ ID NO:1.

6. The polynucleotide of claim 4 which is a cDNA.

7. An isolated and purified single-stranded polynucleotide comprising at least 1200 contiguous nucleotides of a kinase coding sequence or a complement of the coding sequence for an amino acid sequence shown in SEQ ID NO:2.

8. The polynucleotide of claim 7 wherein the protein comprises the amino acid sequence shown in SEQ ID NO:2 the coding sequence comprises the nucleotide sequence shown in SEQ ID NO:1.

9. An expression construct, comprising;
a coding sequence for the amino acid sequence shown in SEQ ID NO:2
a promoter which is located upstream from the coding sequence and which controls expression of the coding sequence.

10. The expression construct of claim 9 wherein the coding sequence comprises the nucleotide sequence shown in SEQ ID NO:1.

11. A host cell comprising an expression construct, wherein the expression construct comprises:
a coding sequence for a protein comprising the amino acid sequence shown in SEQ ID NO:2
a promoter which is located upstream from the coding sequence and which controls expression of the coding sequence.

12. The host cell of claim 11 which is prokaryotic.

13. The host cell of claim 11 which is eukaryotic.

14. A method of producing a protein, comprising the steps of:
culturing a host cell in a culture medium, wherein the host cell comprises an expression construct comprising (a) a coding sequence for a protein comprising the amino acid sequence shown in SEQ ID NO:2 (b) a promoter which is located upstream from the coding sequence and which controls expression of the coding sequence, wherein the step of culturing is carried out under conditions whereby the protein is expressed; and
recovering the protein.

15. A composition comprising:
a protein comprising the amino acid sequence shown in SEQ ID NO:2
a pharmaceutically acceptable carrier.

16. A composition comprising:
a polynucleotide encoding a protein comprising the amino acid sequence shown in SEQ ID NO:2
a pharmaceutically acceptable carrier.

17. The composition of claim 16 wherein the polynucleotide comprises the nucleotide sequence shown in SEQ ID NO:1.

* * * * *

UNITED STATES PATENT AND TRADEMARK OFFICE
CERTIFICATE OF CORRECTION

PATENT NO. : 7,052,892 B2  Page 1 of 1
APPLICATION NO. : 10/470726
DATED : May 30, 2006
INVENTOR(S) : Rainer H. Köhler It is certified that error appears in the above-identified patent and that said Letters Patent is hereby corrected as shown below:

On the cover page, United States Patent section (12):
    Please replace "Rainer" with --Köhler--

On the cover page, Inventors section (75):
    Please replace "Köhler H. Rainer" with --Rainer H. Köhler--

In Column 73, Claim 3, Line 39:
    Please replace "as" with --in--

In Column 73, Claim 9, Line 57:
    Please replace "NO:2" with --NO:2; and--

In Column 74, Claim 11, Line 32:
    Please replace "in SEC IN NO:2" with --as SEQ ID NO:2; and--

In Column 74, Claim 14, Line 43:
    Please replace "in" with --as--

In Column 74, Claim 15, Line 50:
    Please replace "in" with --as--

In Column 74, Claim 15, Line 51:
    Please replace "NO:2" with --NO:2; and--

In Column 74, Claim 17, Line 59:
    Please replace "in" with --as--

Signed and Sealed this

Fourteenth Day of November, 2006

JON W. DUDAS
*Director of the United States Patent and Trademark Office*

SEQUENCE LISTING

<160> NUMBER OF SEQ ID NOS: 11

<210> SEQ ID NO 1
<211> LENGTH: 1677
<212> TYPE: DNA
<213> ORGANISM: Homo sapiens
<220> FEATURE:
<221> NAME/KEY: CDS
<222> LOCATION: (1)..(1677)
<223> OTHER INFORMATION:

<400> SEQUENCE: 1

```
atg gat gac aaa gat att gac aaa gaa cta agg cag aaa tta aac ttt        48
Met Asp Asp Lys Asp Ile Asp Lys Glu Leu Arg Gln Lys Leu Asn Phe
1               5                   10                  15 tcc tat tgt gag gag act gag att gaa ggg cag aag aaa gta gaa gaa        96
Ser Tyr Cys Glu Glu Thr Glu Ile Glu Gly Gln Lys Lys Val Glu Glu
                20                  25                  30 agc agg gag gct tcg agc caa acc cca gag aag ggt gaa gtg cag gat       144
Ser Arg Glu Ala Ser Ser Gln Thr Pro Glu Lys Gly Glu Val Gln Asp
            35                  40                  45 tca gag gca aag ggt aca cca cct tgg act ccc ctt agc aac gtg cat       192
Ser Glu Ala Lys Gly Thr Pro Pro Trp Thr Pro Leu Ser Asn Val His
        50                  55                  60 gag ctc gac aca tct tcg gaa aaa gac aaa gaa agt cca gat cag att       240
Glu Leu Asp Thr Ser Ser Glu Lys Asp Lys Glu Ser Pro Asp Gln Ile
65                  70                  75                  80 ttg agg act cca gtg tca cac cct ctc aaa tgt cct gag aca cca gcc       288
Leu Arg Thr Pro Val Ser His Pro Leu Lys Cys Pro Glu Thr Pro Ala
                85                  90                  95 caa cca gac agc agg agc aag ctg ctg ccc agt gac agc ccc tct act       336
Gln Pro Asp Ser Arg Ser Lys Leu Leu Pro Ser Asp Ser Pro Ser Thr
                100                 105                 110 ccc aaa acc atg ctg agc cgg ttg gtg att tct cca aca ggg aag ctt       384
Pro Lys Thr Met Leu Ser Arg Leu Val Ile Ser Pro Thr Gly Lys Leu
            115                 120                 125 cct tcc aga ggc cct aag cat ttg aag ctc aca cct gct ccc ctc aag       432
Pro Ser Arg Gly Pro Lys His Leu Lys Leu Thr Pro Ala Pro Leu Lys
        130                 135                 140
```

```
gat gag atg acc tca ttg gct ctg gtc aat att aat ccc ttc act cca         480
Asp Glu Met Thr Ser Leu Ala Leu Val Asn Ile Asn Pro Phe Thr Pro
145                 150                 155                 160 gag tcc tat aaa aaa tta ttt ctt caa tct ggt ggc aag agg aaa ata         528
Glu Ser Tyr Lys Lys Leu Phe Leu Gln Ser Gly Gly Lys Arg Lys Ile
                165                 170                 175 aga gga gat ctt gag gaa gct ggt cca gag gaa ggc aag gga ggg ctg         576
Arg Gly Asp Leu Glu Glu Ala Gly Pro Glu Glu Gly Lys Gly Gly Leu
            180                 185                 190 cct gcc aag aga tgt gtt tta cga gaa acc aac atg gct tcc cgc tat         624
Pro Ala Lys Arg Cys Val Leu Arg Glu Thr Asn Met Ala Ser Arg Tyr
        195                 200                 205 gaa aaa gaa ttc ttg gag gtt gaa aaa att ggg gtt ggc gaa ttt ggt         672
Glu Lys Glu Phe Leu Glu Val Glu Lys Ile Gly Val Gly Glu Phe Gly
    210                 215                 220 aca gtc tac aag tgc att aag agg ctg gat gga tgt gtt tat gca ata         720
Thr Val Tyr Lys Cys Ile Lys Arg Leu Asp Gly Cys Val Tyr Ala Ile
225                 230                 235                 240 aag cgc tct atg aaa act ttt aca gaa tta tca aat gag aat tcg gct         768
Lys Arg Ser Met Lys Thr Phe Thr Glu Leu Ser Asn Glu Asn Ser Ala
                245                 250                 255 ttg cat gaa gtt tat gct cac gca gtg ctt ggg cat cac ccc cat gtg         816
Leu His Glu Val Tyr Ala His Ala Val Leu Gly His His Pro His Val
            260                 265                 270 gta cgt tac tat tcc tca tgg gca gaa gat gac cac atg atc att cag         864
Val Arg Tyr Tyr Ser Ser Trp Ala Glu Asp Asp His Met Ile Ile Gln
        275                 280                 285 aat gaa tac tgc aat ggt ggg agt ttg caa gct gct ata tct gaa aac         912
Asn Glu Tyr Cys Asn Gly Gly Ser Leu Gln Ala Ala Ile Ser Glu Asn
    290                 295                 300 act aag tct ggc aat cat ttt gaa gag cca aaa ctc aag gac atc ctt         960
Thr Lys Ser Gly Asn His Phe Glu Glu Pro Lys Leu Lys Asp Ile Leu
305                 310                 315                 320 cta cag att tcc ctt ggc ctt aat tac atc cac aac tct agc atg gta        1008
Leu Gln Ile Ser Leu Gly Leu Asn Tyr Ile His Asn Ser Ser Met Val
                325                 330                 335 cac ctg gac atc aaa cct agt aat ata ttc att tgt cac aag atg caa        1056
His Leu Asp Ile Lys Pro Ser Asn Ile Phe Ile Cys His Lys Met Gln
            340                 345                 350 agt gaa tcc tct gga gtc ata gaa gaa gtt gaa aat gaa gct gat tgg        1104
Ser Glu Ser Ser Gly Val Ile Glu Glu Val Glu Asn Glu Ala Asp Trp
        355                 360                 365 ttt ctc tct gcc aat gtg atg tat aaa att ggt gac ctg ggc cac gca        1152
Phe Leu Ser Ala Asn Val Met Tyr Lys Ile Gly Asp Leu Gly His Ala
    370                 375                 380 aca tca ata aac aaa ccc aaa gtg gaa gaa gga gat agt cgc ttc ctg        1200
Thr Ser Ile Asn Lys Pro Lys Val Glu Glu Gly Asp Ser Arg Phe Leu
385                 390                 395                 400 gct aat gag att ttg caa gag gat tac cgg cac ctt ccc aaa gca gac        1248
Ala Asn Glu Ile Leu Gln Glu Asp Tyr Arg His Leu Pro Lys Ala Asp
                405                 410                 415 ata ttt gcc ttg gga tta aca att gca gtg gct gca gga gca gag tca        1296
Ile Phe Ala Leu Gly Leu Thr Ile Ala Val Ala Ala Gly Ala Glu Ser
            420                 425                 430 ttg ccc acc aat ggt gct gca tgg cac cat atc cgc aag ggt aac ttt        1344
Leu Pro Thr Asn Gly Ala Ala Trp His His Ile Arg Lys Gly Asn Phe
        435                 440                 445 ccg gac gtt cct cag gag ctc tca gaa agc ttt tcc agt ctg ctc aag        1392
Pro Asp Val Pro Gln Glu Leu Ser Glu Ser Phe Ser Ser Leu Leu Lys
    450                 455                 460
```

-continued

```
aac atg atc caa cct gat gcc gaa cag aga cct tct gca gca gct ctg    1440
Asn Met Ile Gln Pro Asp Ala Glu Gln Arg Pro Ser Ala Ala Ala Leu
465                 470                 475                 480 gcc aga aat aca gtt ctc cgg cct tcc ctg gga aaa aca gaa gag ctc    1488
Ala Arg Asn Thr Val Leu Arg Pro Ser Leu Gly Lys Thr Glu Glu Leu
                485                 490                 495 caa cag cag ctg aat ttg gaa aag ttc aag act gcc aca ctg gaa agg    1536
Gln Gln Gln Leu Asn Leu Glu Lys Phe Lys Thr Ala Thr Leu Glu Arg
            500                 505                 510 gaa ctg aga gaa gcc cag cag gcc cag tca ccc cag gga tat acc cat    1584
Glu Leu Arg Glu Ala Gln Gln Ala Gln Ser Pro Gln Gly Tyr Thr His
        515                 520                 525 cat ggt gac act ggg gtc tct ggg acc cac aca gga tca aga agc aca    1632
His Gly Asp Thr Gly Val Ser Gly Thr His Thr Gly Ser Arg Ser Thr
    530                 535                 540 aaa cgc ctg gtg gga gga aag agt gca agg tct tca agc ttt acc        1677
Lys Arg Leu Val Gly Gly Lys Ser Ala Arg Ser Ser Ser Phe Thr
545                 550                 555
```

<210> SEQ ID NO 2
<211> LENGTH: 559
<212> TYPE: PRT
<213> ORGANISM: Homo sapiens

<400> SEQUENCE: 2

```
Met Asp Asp Lys Asp Ile Asp Lys Glu Leu Arg Gln Lys Leu Asn Phe
1               5                   10                  15

Ser Tyr Cys Glu Glu Thr Glu Ile Glu Gly Gln Lys Lys Val Glu Glu
                20                  25                  30

Ser Arg Glu Ala Ser Ser Gln Thr Pro Glu Lys Gly Glu Val Gln Asp
            35                  40                  45

Ser Glu Ala Lys Gly Thr Pro Pro Trp Thr Pro Leu Ser Asn Val His
        50                  55                  60

Glu Leu Asp Thr Ser Ser Glu Lys Asp Lys Glu Ser Pro Asp Gln Ile
65                  70                  75                  80

Leu Arg Thr Pro Val Ser His Pro Leu Lys Cys Pro Glu Thr Pro Ala
                85                  90                  95

Gln Pro Asp Ser Arg Ser Lys Leu Leu Pro Ser Asp Ser Pro Ser Thr
            100                 105                 110

Pro Lys Thr Met Leu Ser Arg Leu Val Ile Ser Pro Thr Gly Lys Leu
        115                 120                 125

Pro Ser Arg Gly Pro Lys His Leu Lys Leu Thr Pro Ala Pro Leu Lys
    130                 135                 140

Asp Glu Met Thr Ser Leu Ala Leu Val Asn Ile Asn Pro Phe Thr Pro
145                 150                 155                 160

Glu Ser Tyr Lys Lys Leu Phe Leu Gln Ser Gly Gly Lys Arg Lys Ile
                165                 170                 175

Arg Gly Asp Leu Glu Glu Ala Gly Pro Glu Glu Gly Lys Gly Gly Leu
            180                 185                 190

Pro Ala Lys Arg Cys Val Leu Arg Glu Thr Asn Met Ala Ser Arg Tyr
        195                 200                 205

Glu Lys Glu Phe Leu Glu Val Glu Lys Ile Gly Val Gly Glu Phe Gly
    210                 215                 220

Thr Val Tyr Lys Cys Ile Lys Arg Leu Asp Gly Cys Val Tyr Ala Ile
225                 230                 235                 240

Lys Arg Ser Met Lys Thr Phe Thr Glu Leu Ser Asn Glu Asn Ser Ala
```

```
                245                 250                 255
Leu His Glu Val Tyr Ala His Ala Val Leu Gly His His Pro His Val
            260                 265                 270

Val Arg Tyr Tyr Ser Ser Trp Ala Glu Asp His Met Ile Ile Gln
        275                 280                 285

Asn Glu Tyr Cys Asn Gly Gly Ser Leu Gln Ala Ala Ile Ser Glu Asn
    290                 295                 300

Thr Lys Ser Gly Asn His Phe Glu Glu Pro Lys Leu Lys Asp Ile Leu
305                 310                 315                 320

Leu Gln Ile Ser Leu Gly Leu Asn Tyr Ile His Asn Ser Ser Met Val
            325                 330                 335

His Leu Asp Ile Lys Pro Ser Asn Ile Phe Ile Cys His Lys Met Gln
        340                 345                 350

Ser Glu Ser Ser Gly Val Ile Glu Glu Val Glu Asn Glu Ala Asp Trp
    355                 360                 365

Phe Leu Ser Ala Asn Val Met Tyr Lys Ile Gly Asp Leu Gly His Ala
            370                 375                 380

Thr Ser Ile Asn Lys Pro Lys Val Glu Gly Asp Ser Arg Phe Leu
385                 390                 395                 400

Ala Asn Glu Ile Leu Gln Glu Asp Tyr Arg His Leu Pro Lys Ala Asp
            405                 410                 415

Ile Phe Ala Leu Gly Leu Thr Ile Ala Val Ala Ala Gly Ala Glu Ser
        420                 425                 430

Leu Pro Thr Asn Gly Ala Ala Trp His His Ile Arg Lys Gly Asn Phe
    435                 440                 445

Pro Asp Val Pro Gln Glu Leu Ser Glu Ser Phe Ser Ser Leu Leu Lys
450                 455                 460

Asn Met Ile Gln Pro Asp Ala Glu Gln Arg Pro Ser Ala Ala Leu
465                 470                 475                 480

Ala Arg Asn Thr Val Leu Arg Pro Ser Leu Gly Lys Thr Glu Glu Leu
            485                 490                 495

Gln Gln Gln Leu Asn Leu Glu Lys Phe Lys Thr Ala Thr Leu Glu Arg
        500                 505                 510

Glu Leu Arg Glu Ala Gln Gln Ala Gln Ser Pro Gln Gly Tyr Thr His
    515                 520                 525

His Gly Asp Thr Gly Val Ser Gly Thr His Thr Gly Ser Arg Ser Thr
530                 535                 540

Lys Arg Leu Val Gly Gly Lys Ser Ala Arg Ser Ser Ser Phe Thr
545                 550                 555

<210> SEQ ID NO 3
<211> LENGTH: 555
<212> TYPE: PRT
<213> ORGANISM: Xenopus laevis

<400> SEQUENCE: 3

Met Arg Thr Ala Met Ser Cys Gly Gly Gly Leu Val Gln Arg Leu Asp
1               5                   10                  15

Phe Ser Ser Ser Asp Glu Glu Asp Gly Leu Ser Asn Gly Ile Asn Glu
            20                  25                  30

Gly Pro Gln Lys Gly Ser Pro Val Ser Ser Trp Arg Thr Asn Asn Cys
        35                  40                  45

Pro Phe Pro Ile Thr Pro Gln Arg Asn Glu Arg Glu Leu Ser Pro Thr
    50                  55                  60
```

-continued

```
Gln Glu Leu Ser Pro Ser Ser Asp Tyr Ser Pro Asp Pro Ser Val Gly
 65                  70                  75                  80

Ala Glu Cys Pro Gly Thr Pro Leu His Tyr Ser Thr Trp Lys Lys Leu
                 85                  90                  95

Lys Leu Cys Asp Thr Pro Tyr Thr Pro Lys Ser Leu Leu Tyr Lys Thr
                100                 105                 110

Leu Pro Ser Pro Gly Ser Arg Val His Cys Arg Gly Gln Arg Leu Leu
                115                 120                 125

Arg Phe Val Ala Gly Thr Gly Ala Glu Leu Asp Asp Pro Ser Leu Val
    130                 135                 140

Asn Ile Asn Pro Phe Thr Pro Glu Ser Tyr Arg Gln Thr His Phe Gln
145                 150                 155                 160

Pro Asn Gly Lys Arg Lys Glu Arg Pro Glu Asp Asp Cys Arg Thr Asp
                165                 170                 175

Arg Gln Met Lys Tyr Ala Glu Lys Glu His Pro Ala Val Phe Gln Ser
                180                 185                 190

Lys Arg Phe Val Leu Arg Glu Thr Asn Met Gly Ser Arg Tyr Lys Thr
            195                 200                 205

Glu Phe Leu Glu Ile Glu Lys Ile Gly Ala Gly Glu Phe Gly Ser Val
    210                 215                 220

Phe Lys Cys Val Lys Arg Leu Asp Gly Cys Phe Tyr Ala Ile Lys Arg
225                 230                 235                 240

Ser Lys Lys Pro Leu Ala Gly Ser Thr Asp Glu Gln Leu Ala Leu Arg
                245                 250                 255

Glu Val Tyr Ala His Ala Val Leu Gly His His Pro His Val Val Arg
                260                 265                 270

Tyr Tyr Ser Ala Trp Ala Glu Asp Asp His Met Ile Ile Gln Asn Glu
            275                 280                 285

Tyr Cys Asn Gly Gly Ser Leu Gln Asp Leu Ile Val Asp Asn Asn Lys
    290                 295                 300

Glu Gly Gln Phe Val Leu Glu Gln Glu Leu Lys Glu Ile Leu Leu Gln
305                 310                 315                 320

Val Ser Met Gly Leu Lys Tyr Ile His Gly Ser Gly Leu Val His Met
                325                 330                 335

Asp Ile Lys Pro Ser Asn Ile Phe Ile Cys Arg Lys Gln Thr Glu Leu
                340                 345                 350

Gly Gln Glu Glu Ser Asp Gly Glu Asp Asp Leu Ser Ser Gly Ser Val
            355                 360                 365

Leu Tyr Lys Ile Gly Asp Leu Gly His Val Thr Ser Ile Leu Asn Pro
    370                 375                 380

Gln Val Glu Glu Gly Asp Ser Arg Phe Leu Ala Asn Glu Ile Leu Gln
385                 390                 395                 400

Glu Asp Tyr Ser Gln Leu Pro Lys Ala Asp Ile Phe Ala Leu Gly Leu
                405                 410                 415

Thr Ile Ala Leu Ala Ala Gly Ala Pro Leu Pro Cys Asn Gly Glu Asp
                420                 425                 430

Ser Trp His His Ile Arg Lys Gly Asn Leu Pro His Val Pro Gln Leu
            435                 440                 445

Leu Thr Pro Val Phe Leu Ala Leu Leu Lys Leu Leu Val His Pro Asp
    450                 455                 460

Pro Val Met Arg Pro Pro Ala Ala Ser Leu Ala Lys Asn Ser Val Leu
465                 470                 475                 480

Arg Arg Cys Val Gly Lys Ala Ala Gln Leu Gln Lys Gln Leu Asn Val
```

```
                   485                 490                 495
Glu Lys Phe Lys Thr Ala Met Leu Glu Arg Glu Leu Lys Ala Ala Lys
            500                 505                 510

Leu Ala Gln Thr Ser Gly Lys Asp Glu Cys Ser Asp Leu Pro Pro Met
            515                 520                 525

Ser Gly Phe Ser Cys Arg Gly Arg Lys Arg Leu Val Gly Ala Lys Asn
            530                 535                 540

Thr Arg Ser Leu Ser Phe Thr Cys Gly Gly Tyr
545                 550                 555

<210> SEQ ID NO 4
<211> LENGTH: 338
<212> TYPE: DNA
<213> ORGANISM: Homo sapiens

<400> SEQUENCE: 4
tttgagatag tgattttatt tcctttggct atataactgg aagagaagag ggacagcttg    60
attgtataat agttgttttt ttcttcaaag agttttccat ccttctcatc ggggcttctc   120
ttttgtcatc ctcattcaga ccatgctgag ccggttggtg atttctccaa cagggaagct   180
tccttccaga ggccctaagc atttgaagct cacacctgct cccctcaagg atgagatgac   240
ctcattggct ctggtcaata ttaatccctt cactccagag tcctataaaa aattatttct   300
tcaatatcta tcctgtcatt ttttttttcag gtaatata                          338

<210> SEQ ID NO 5
<211> LENGTH: 2358
<212> TYPE: DNA
<213> ORGANISM: Homo sapiens

<400> SEQUENCE: 5
atggatgaca aagatattga caaagaacta aggcagaaat taaacttttc ctattgtgag    60
gagactgaga ttgaagggca gaagaaagta gaagaaagca gggaggcttc gagccaaacc   120
ccagagaagg gtgaagtgca ggattcagag gcaaagggta caccaccttg gactcccctt   180
agcaacgtgc atgagctcga cacatcttcg gaaaaagaca agaaagtcc agatcagatt    240 ttgaggactc cagtgtcaca ccctctcaaa tgtcctgaga caccagccca accagacagc   300
aggagcaagc tgctgcccag tgacagcccc tctactccca aaaccatgct gagccggttg   360
gtgatttctc caacagggaa gcttccttcc agaggccta agcatttgaa gctcacacct    420
gctcccctca aggatgagat gacctcattg gctctggtca atattaatcc cttcactcca   480
gagtcctata aaaaattatt tcttcaatct ggtggcaaga ggaaaataag aggagatctt   540
gaggaagctg gtccagagga aggcaaggga gggctgcctg ccaagagatg tgttttacga   600
gaaaccaaca tggcttcccg ctatgaaaaa gaattcttgg aggttgaaaa aattggggtt   660
ggcgaatttg gtacagtcta caagtgcatt aagaggctgg atggatgtgt ttatgcaata   720
aagcgctcta tgaaaactt tacagaatta tcaaatgaga attcggcttt gcatgaagtt   780
tatgctcacg cagtgcttgg gcatcacccc catgtggtac gttactattc ctcatgggca   840
gaagatgacc acatgatcat tcagaatgaa tactgcaatg gtgggagttt gcaagctgct   900
atatctgaaa acactaagtc tggcaatcat tttgagagc caaaactcaa ggacatcctt   960
ctacagattt ccctttggcc taattacatc cacaactcta gcatggtaca cctggacatc  1020
aaacctagta atatattcat ttgtcacaag atgcaaagtg aatcctctgg agtcatagaa  1080
gaagttgaaa atgaagctga ttggttttct ctgccaatg tgatgtataa aattggtgac  1140
```

-continued

```
ctgggccacg caacatcaat aaacaaaccc aaagtggaag aaggagatag tcgcttcctg    1200
gctaatgaga ttttgcaaga ggattaccgg caccttccca aagcagacat atttgccttg    1260
ggattaacaa ttgcagtggc tgcaggagca gagtcattgc ccaccaatgg tgctgcatgg    1320
caccatatcc gcaagggtaa cttteeggac gttcctcagg agctctcaga aagcttttcc    1380
agtctgctca agaacatgat ccaacctgat gccgaacaga gacttctgc agcagctctg     1440 gccagaaata cagttctccg gccttccctg gaaaaacag aagagctcca acagcagctg     1500
aatttggaaa agttcaagac tgccacactg gaaagggaac tgagagaagc ccagcaggcc    1560
cagtcacccc agggatatac ccatcatggt gacactgggg tctctgggac ccacacagga    1620
tcaagaagca caaacgcct ggtgggagga aagagtgcaa ggtcttcaag ctttacctac     1680
acacagatac ttaccatgaa ttacaatggt ctgcggtatt cagtacagcc ccatgctgtc    1740
aggtttgcag cctggaagca gcaggccaca ccacagagcc gaggtgtgtc caggctccac    1800
catctaggtc gtcaaagtac attctgtggt gttcgtacag caacaaaatc gcctaatgac    1860
gcaatcctca gaccttaccc tgttgttaag gtacttcgtc agtttgtaag acatgagtcc    1920
gaaacaacta ccagtttggt tcttgaaaga tccctgaatc gtgtgcactt acttgggcga    1980
gtgggtcagg accctgtctt gagacaggtg gaaggaaaaa atccagtcac aatattttct    2040
ctagcaacta atgagatgtg gcgatcaggg gatagtgaag tttaccaact gggtgatgtc    2100
agtcaaaaga caacatggca cagaatatca gtattccggc caggcctcag agacgtggca    2160
tatcaatatg tgaaaaaggg gtctcgaatt tatttggaag ggaaaataga ctatggtgaa    2220
tacatggata aaataatgt gaggcgacaa gcaacaacaa tcatagctgg gatcctatct     2280
gtaactaaaa aaccaccacc agtggatggc actcttggct ttttccacag tgatattaat    2340
tcgagtagtt tgttctga                                                  2358
```

<210> SEQ ID NO 6
<211> LENGTH: 785
<212> TYPE: PRT
<213> ORGANISM: Homo sapiens

<400> SEQUENCE: 6

Met Asp Asp Lys Asp Ile Asp Lys Glu Leu Arg Gln Lys Leu Asn Phe
1               5                   10                  15

Ser Tyr Cys Glu Glu Thr Glu Ile Glu Gly Gln Lys Lys Val Glu Glu
                20                  25                  30

Ser Arg Glu Ala Ser Ser Gln Thr Pro Glu Lys Gly Glu Val Gln Asp
            35                  40                  45

Ser Glu Ala Lys Gly Thr Pro Pro Trp Thr Pro Leu Ser Asn Val His
        50                  55                  60

Glu Leu Asp Thr Ser Ser Glu Lys Asp Lys Glu Ser Pro Asp Gln Ile
65                  70                  75                  80

Leu Arg Thr Pro Val Ser His Pro Leu Lys Cys Pro Glu Thr Pro Ala
                85                  90                  95

Gln Pro Asp Ser Arg Ser Lys Leu Leu Pro Ser Asp Ser Pro Ser Thr
            100                 105                 110

Pro Lys Thr Met Leu Ser Arg Leu Val Ile Ser Pro Thr Gly Lys Leu
        115                 120                 125

Pro Ser Arg Gly Pro Lys His Leu Lys Leu Thr Pro Ala Pro Leu Lys
    130                 135                 140

Asp Glu Met Thr Ser Leu Ala Leu Val Asn Ile Asn Pro Phe Thr Pro

-continued

```
            145                 150                 155                 160
        Glu Ser Tyr Lys Lys Leu Phe Leu Gln Ser Gly Gly Lys Arg Lys Ile
                        165                 170                 175

Arg Gly Asp Leu Glu Glu Ala Gly Pro Glu Glu Gly Lys Gly Gly Leu
                        180                 185                 190

Pro Ala Lys Arg Cys Val Leu Arg Glu Thr Asn Met Ala Ser Arg Tyr
                        195                 200                 205

Glu Lys Glu Phe Leu Glu Val Glu Lys Ile Gly Val Gly Glu Phe Gly
                        210                 215                 220

Thr Val Tyr Lys Cys Ile Lys Arg Leu Asp Gly Cys Val Tyr Ala Ile
        225                 230                 235                 240

Lys Arg Ser Met Lys Thr Phe Thr Glu Leu Ser Asn Glu Asn Ser Ala
                        245                 250                 255

Leu His Glu Val Tyr Ala His Ala Val Leu Gly His His Pro His Val
                        260                 265                 270

Val Arg Tyr Tyr Ser Ser Trp Ala Glu Asp His Met Ile Ile Gln
                        275                 280                 285

Asn Glu Tyr Cys Asn Gly Gly Ser Leu Gln Ala Ala Ile Ser Glu Asn
                        290                 295                 300

Thr Lys Ser Gly Asn His Phe Glu Glu Pro Lys Leu Lys Asp Ile Leu
        305                 310                 315                 320

Leu Gln Ile Ser Leu Gly Leu Asn Tyr Ile His Asn Ser Ser Met Val
                        325                 330                 335

His Leu Asp Ile Lys Pro Ser Asn Ile Phe Ile Cys His Lys Met Gln
                        340                 345                 350

Ser Glu Ser Ser Gly Val Ile Glu Val Glu Asn Glu Ala Asp Trp
                        355                 360                 365

Phe Leu Ser Ala Asn Val Met Tyr Lys Ile Gly Asp Leu Gly His Ala
                        370                 375                 380

Thr Ser Ile Asn Lys Pro Lys Val Glu Glu Gly Asp Ser Arg Phe Leu
        385                 390                 395                 400

Ala Asn Glu Ile Leu Gln Glu Asp Tyr Arg His Leu Pro Lys Ala Asp
                        405                 410                 415

Ile Phe Ala Leu Gly Leu Thr Ile Ala Val Ala Ala Gly Ala Glu Ser
                        420                 425                 430

Leu Pro Thr Asn Gly Ala Ala Trp His His Ile Arg Lys Gly Asn Phe
                        435                 440                 445

Pro Asp Val Pro Gln Glu Leu Ser Glu Ser Phe Ser Ser Leu Leu Lys
                        450                 455                 460

Asn Met Ile Gln Pro Asp Ala Glu Gln Arg Pro Ser Ala Ala Leu
        465                 470                 475                 480

Ala Arg Asn Thr Val Leu Arg Pro Ser Leu Gly Lys Thr Glu Glu Leu
                        485                 490                 495

Gln Gln Gln Leu Asn Leu Glu Lys Phe Lys Thr Ala Thr Leu Glu Arg
                        500                 505                 510

Glu Leu Arg Glu Ala Gln Gln Ala Gln Ser Pro Gln Gly Tyr Thr His
                        515                 520                 525

His Gly Asp Thr Gly Val Ser Gly Thr His Thr Gly Ser Arg Ser Thr
                        530                 535                 540

Lys Arg Leu Val Gly Gly Lys Ser Ala Arg Ser Ser Ser Phe Thr Tyr
        545                 550                 555                 560

Thr Gln Ile Leu Thr Met Asn Tyr Asn Gly Leu Arg Tyr Ser Val Gln
                        565                 570                 575
```

-continued

```
Pro His Ala Val Arg Phe Ala Ala Trp Lys Gln Gln Ala Thr Pro Gln
        580                 585                 590
Ser Arg Gly Val Ser Arg Leu His His Leu Gly Arg Gln Ser Thr Phe
        595                 600                 605
Cys Gly Val Arg Thr Ala Thr Lys Ser Pro Asn Asp Ala Ile Leu Arg
        610                 615                 620
Pro Tyr Pro Val Val Lys Val Leu Arg Gln Phe Val Arg His Glu Ser
625                 630                 635                 640
Glu Thr Thr Thr Ser Leu Val Leu Glu Arg Ser Leu Asn Arg Val His
                645                 650                 655
Leu Leu Gly Arg Val Gly Gln Asp Pro Val Leu Arg Gln Val Glu Gly
                660                 665                 670
Lys Asn Pro Val Thr Ile Phe Ser Leu Ala Thr Asn Glu Met Trp Arg
            675                 680                 685
Ser Gly Asp Ser Glu Val Tyr Gln Leu Gly Asp Val Ser Gln Lys Thr
        690                 695                 700
Thr Trp His Arg Ile Ser Val Phe Arg Pro Gly Leu Arg Asp Val Ala
705                 710                 715                 720
Tyr Gln Tyr Val Lys Lys Gly Ser Arg Ile Tyr Leu Glu Gly Lys Ile
                725                 730                 735
Asp Tyr Gly Glu Tyr Met Asp Lys Asn Asn Val Arg Arg Gln Ala Thr
            740                 745                 750
Thr Ile Ile Ala Gly Ile Leu Ser Val Thr Lys Lys Pro Pro Pro Val
        755                 760                 765
Asp Gly Thr Leu Gly Phe Phe His Ser Asp Ile Asn Ser Ser Ser Leu
        770                 775                 780
Phe
785

<210> SEQ ID NO 7
<211> LENGTH: 20
<212> TYPE: DNA
<213> ORGANISM: Homo sapiens
<220> FEATURE:
<221> NAME/KEY: misc_feature
<223> OTHER INFORMATION: Forward primer

<400> SEQUENCE: 7
caggattcag aggcaaaggg                                                  20

<210> SEQ ID NO 8
<211> LENGTH: 26
<212> TYPE: DNA
<213> ORGANISM: Homo sapiens
<220> FEATURE:
<221> NAME/KEY: misc_feature
<223> OTHER INFORMATION: Reverse primer

<400> SEQUENCE: 8
accaccttgg actcccctta gcaacg                                           26

<210> SEQ ID NO 9
<211> LENGTH: 21
<212> TYPE: DNA
<213> ORGANISM: Homo sapiens
<220> FEATURE:
<221> NAME/KEY: misc_feature
<223> OTHER INFORMATION: Fluorogenic probe

<400> SEQUENCE: 9
```

```
cgaagatgtg tcgagctcat g                                            21

<210> SEQ ID NO 10
<211> LENGTH: 22
<212> TYPE: DNA
<213> ORGANISM: Homo sapiens
<220> FEATURE:
<221> NAME/KEY: misc_feature
<223> OTHER INFORMATION: Forward prmer 2

<400> SEQUENCE: 10
tccagtgtca caccctctca aa                                           22

<210> SEQ ID NO 11
<211> LENGTH: 19
<212> TYPE: DNA
<213> ORGANISM: Homo sapiens
<220> FEATURE:
<221> NAME/KEY: misc_feature
<223> OTHER INFORMATION: Reverse primer 2

<400> SEQUENCE: 11
tgtcactggg cagcagctt                                               19
```